US009596224B2

(12) United States Patent
Woods et al.

(10) Patent No.: US 9,596,224 B2
(45) Date of Patent: Mar. 14, 2017

(54) SYSTEMS, DEVICES, COMPONENTS AND METHODS FOR COMMUNICATING WITH AN IMD USING A PORTABLE ELECTRONIC DEVICE AND A MOBILE COMPUTING DEVICE

(71) Applicant: Nuvectra Corporation, Plano, TX (US)

(72) Inventors: Thomas F. Woods, Lyons, CO (US); Norbert Kaula, Arvada, CO (US); Yohannes Iyassu, Denver, CO (US)

(73) Assignee: Nuvectra Corporation, Plano, TX (US)

( * ) Notice: Subject to any disclaimer, the term of this patent is extended or adjusted under 35 U.S.C. 154(b) by 397 days.

(21) Appl. No.: 14/245,225

(22) Filed: Apr. 4, 2014

(65) Prior Publication Data

US 2014/0304773 A1 Oct. 9, 2014

Related U.S. Application Data

(60) Provisional application No. 61/809,223, filed on Apr. 5, 2013, provisional application No. 61/824,296, filed on May 16, 2013.

(51) Int. Cl.
*H04L 29/06* (2006.01)
*A61N 1/372* (2006.01)
*H04L 29/08* (2006.01)
*A61B 5/00* (2006.01)

(52) U.S. Cl.
CPC .......... *H04L 63/08* (2013.01); *A61N 1/37247* (2013.01); *A61B 5/002* (2013.01); *A61B 5/0031* (2013.01); *H04L 63/083* (2013.01); *H04L 63/0861* (2013.01); *H04L 67/12* (2013.01)

(58) Field of Classification Search
CPC ..... H04L 63/08; H04L 63/0861; H04L 67/12; H04L 63/083; A61N 1/37247; A61B 5/002; A61B 5/0031
See application file for complete search history.

(56) References Cited

U.S. PATENT DOCUMENTS

| 4,432,360 | A | 2/1984 | Mumford et al. |
| 6,564,104 | B2 | 5/2003 | Nelson et al. |
| 6,961,448 | B2 | 11/2005 | Nichols et al. |
| 7,003,349 | B1 | 2/2006 | Andersson et al. |
| 7,778,710 | B2 | 8/2010 | Propato |
| 7,801,596 | B2 | 9/2010 | Fischell et al. |

(Continued)

FOREIGN PATENT DOCUMENTS

EP  2 587 394 A1  5/2013

*Primary Examiner* — Jeffrey Pwu
*Assistant Examiner* — William Corum, Jr.
(74) *Attorney, Agent, or Firm* — Haynes and Boone, LLP; Eric Li

(57) ABSTRACT

The present disclosure involves a method of communicating with an implantable medical device. An authentication process is performed to verify an identity of a user of a mobile computing device. A request is received from the user to access an implantable medical device via the mobile computing device. Based on the identity of the user, a first user interface suitable for the user is selected from a plurality of user interfaces that are each configured to control an implantable medical device. The plurality of user interfaces have different visual characteristics and different levels of access to the implantable medical device. The first user interface is displayed on the mobile computing device.

36 Claims, 22 Drawing Sheets

(56) References Cited

U.S. PATENT DOCUMENTS

| | | |
|---|---|---|
| 7,805,199 B2 | 9/2010 | KenKnight et al. |
| 7,890,180 B2 | 2/2011 | Quiles et al. |
| 2003/0177031 A1 | 9/2003 | Malek |
| 2005/0261934 A1* | 11/2005 | Thompson ......... A61N 1/37282 705/2 |
| 2006/0212092 A1* | 9/2006 | Pless ................. A61N 1/36064 607/45 |
| 2007/0078497 A1 | 4/2007 | Vandanacker |
| 2008/0140161 A1 | 6/2008 | Goetz et al. |
| 2010/0058462 A1 | 3/2010 | Chow |
| 2010/0222845 A1 | 9/2010 | Goetz |
| 2010/0274324 A1* | 10/2010 | Bennett ............. A61N 1/37247 607/60 |
| 2011/0015496 A1 | 1/2011 | Sherman et al. |
| 2011/0015693 A1 | 1/2011 | Williamson |
| 2011/0172737 A1 | 7/2011 | Davis et al. |
| 2011/0172744 A1 | 7/2011 | Davis et al. |
| 2012/0163663 A1* | 6/2012 | Masoud et al. ............... 382/103 |
| 2012/0166680 A1 | 6/2012 | Masoud et al. |
| 2012/0215285 A1* | 8/2012 | Tahmasian et al. ........... 607/59 |
| 2012/0266221 A1* | 10/2012 | Castelluccia et al. ............ 726/6 |
| 2013/0047233 A1* | 2/2013 | Fisk et al. ......................... 726/7 |
| 2013/0132855 A1* | 5/2013 | Manicka et al. ............. 715/740 |
| 2013/0138452 A1 | 5/2013 | Cork et al. |

* cited by examiner

SYSTEMS, DEVICES, COMPONENTS AND METHODS FOR COMMUNICATING WITH AN IMD USING A PORTABLE ELECTRONIC DEVICE AND A MOBILE COMPUTING DEVICE

PRIORITY DATA

The present application is a utility application of provisional U.S. Patent Application No. 61/809,223, filed on Apr. 5, 2013, entitled "Systems, Devices, Components and Methods for Communicating with an IMD Using an External Communication Device and a Mobile Phone," and a utility application of provisional U.S. Patent Application No. 61/824,296, filed on May 16, 2013, entitled "Features and Functionalities of an Advanced Clinician Programmer," the disclosures of each of which are hereby incorporated by reference in their respective entireties.

FIELD

Various embodiments described herein relate to the field of IMDs, and methods of communicating therewith.

BACKGROUND

As medical device technologies continue to evolve, IMDs (IMDs) have gained increasing popularity in the medical field. For example, one type of implanted medical device includes implantable pulse generators, which are designed to deliver electrical stimulation to a patient. Through proper electrical stimulation, the implantable pulse generators can provide pain relief for patients or restore bodily functions. Examples of some types of IMDs include pacemakers, implantable cardioverter-defibrillators, implantable cardiac signal monitors, implantable loop recorders, implantable spinal cord stimulators, implantable pelvic nerve stimulators, implantable peripheral nerve stimulators, implantable brain stimulators, gastric system stimulators, and so on.

Communication with IMDs is generally accomplished by external clinician programmers (CPs), or by external patient programmers or monitors (PPs). However, conventional CPs and PPs are generally expensive, bulky, have limited functionalities, may be difficult to replace, require extensive training for proper use, and as dedicated devices typically tied to one or more families of IMDs, usually become outmoded and outdated quickly due to the on-going rapid pace of computer hardware and software innovation.

As a result, although existing systems and methods of communicating with IMDs have been generally adequate for their intended purposes, they have not been entirely satisfactory in every aspect.

SUMMARY

One aspect of the present disclosure involves a medical system. The medical system includes an implantable medical device, a mobile computing device, and a portable electronic device. The mobile computing device including a screen. The mobile computing device is configured to display on the screen: in response to an authentication of a first user, a first user interface for controlling the implantable medical device based on one or more first commands received from the first user. The mobile computing device is configured to display on the screen: in response to an authentication of a second user, a second user interface for controlling the implantable medical device based on one or more second commands received from the second user. The first user interface and the second user interface have different visual appearances. The first and second user interfaces are associated with different levels of access to the implantable medical device. The portable electronic device includes: a first communications component configured to conduct telecommunications with the implantable medical device under a first communications protocol; and a second communications component configured to conduct telecommunications with the mobile computing device under a second communications protocol different from the first communications protocol. The portable electronic device is configured to use the first and second communications components to relay the one or more first commands or the one or more second commands to the implantable medical device.

Another aspect of the present disclosure involves a portable electronic apparatus for facilitating communication between an implantable medical device and a mobile computing device. The portable apparatus includes: a first communications component configured to conduct telecommunications with the implantable medical device under a first communications protocol; a second communications component configured to conduct telecommunications with the mobile computing device under a second communications protocol different from the first communications protocol; a memory component configured to store programming instructions; and a processor component configured to execute the programming instructions to perform the following steps: selecting, based on an authentication of a first user, a first user interface for controlling the implantable medical device; and selecting, based on an authentication of a second user, a second user interface for controlling the implantable medical device. The first user interface and the second user interface have different visual appearances and different levels of access to the implantable medical device.

Yet another aspect of the present disclosure involves a method of communicating with an implantable medical device. The method includes the following steps: performing an authentication process to verify an identity of a user of a mobile computing device; receiving a request from the user to access an implantable medical device via the mobile computing device; selecting, based on the identity of the user, a first user interface suitable for the user from a plurality of user interfaces that are each configured to control an implantable medical device, wherein the plurality of user interfaces have different visual characteristics and different levels of access to the implantable medical device; and displaying the first user interface on the mobile computing device.

One more aspect of the present disclosure involves a non-transitory computer readable medium comprising executable instructions that when executed by a processor, causes the processor to perform the steps of: performing an authentication process to verify an identity of a user of a mobile computing device; receiving a request from the user to access an implantable medical device via the mobile computing device; selecting, based on the identity of the user, a first user interface suitable for the user from a plurality of user interfaces that are each configured to control an implantable medical device, wherein the plurality of user interfaces have different visual characteristics and different levels of access to the implantable medical device; and displaying the first user interface on the mobile computing device.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In the figures, elements having the same designation have the same or similar functions.

DETAILED DESCRIPTION

Figure 1:
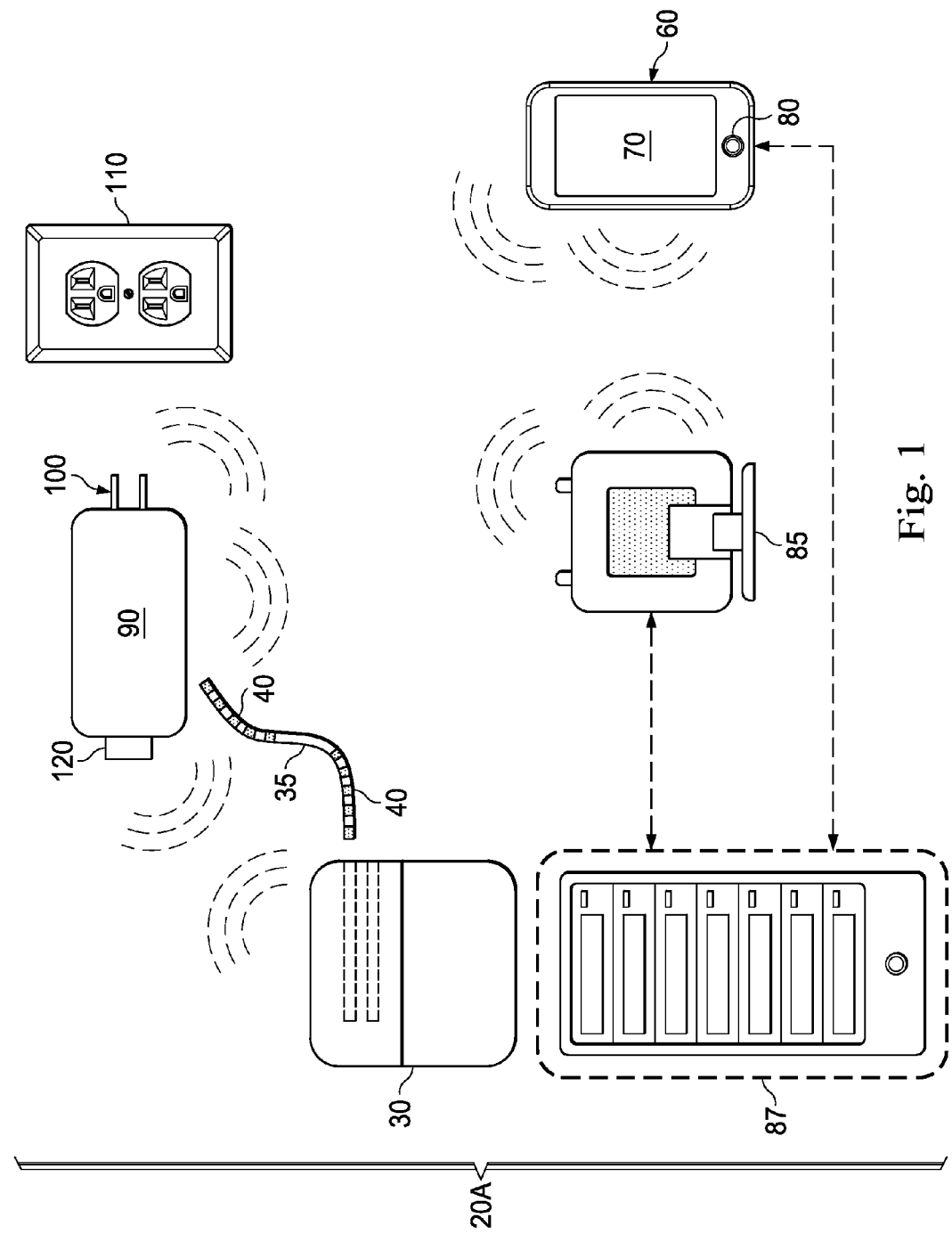
FIGS. 1-3 and 14-15 are simplified block diagrams of example medical systems according to various embodiments of the present disclosure.

It is to be understood that the following disclosure provides many different embodiments, or examples, for implementing different features of the invention. Specific examples of components and arrangements are described below to simplify the present disclosure. These are, of course, merely examples and are not intended to be limiting. Various features may be arbitrarily drawn to different scales for simplicity and clarity.

The use of IMDs (IMDs) has become increasingly prevalent over time. Some of these IMDs include pulse generators that are capable of providing pain relief by delivering electrical stimulation to a patient. Other examples of IMDs include pacemakers, implantable cardioverter-defibrillators, implantable cardiac signal monitors, implantable loop recorders, implantable spinal cord stimulators, implantable pelvic nerve stimulators, implantable peripheral nerve stimulators, implantable brain stimulators, and gastric system stimulators, etc.

Electronic programmers have been used to configure or program these IMDs so that they can be operated in a certain manner. These electronic programmers include clinician programmers (CPs) and patient programmers (PPs), each of which may be a handheld device. For example, in the case of a pulse generator as an IMD, a clinician programmer allows a medical professional (e.g., a doctor or a nurse) to define the particular electrical stimulation therapy to be delivered by the pulse generator to a target area of the patient's body, while a patient programmer allows a patient to alter one or more parameters of the electrical stimulation therapy.

In recent years, such electronic programmers have achieved significant improvements, for example, improvements in size, power consumption, lifetime, and ease of use. Nevertheless, there are still numerous drawbacks related to using such electronic programmers. For example, electronic programmers are generally expensive. They also tend to be limited in the types of communication functions they are capable of performing (e.g., communication with the IMD is only possible with a CP or PP). In addition, if electronic programmers are lost or become defective, it may be difficult or at least time consuming to find a replacement. Moreover, programmers are typically not configured to alert a health care provider or the patient that an adverse event or a device malfunction has been detected by the IMD when the patient is not in the health care provider's office, or when the PP is not positioned over the IMD and in communication therewith. The prior art relating to the topic of patient monitoring and automatic alerts generated by IMDs for dissemination to patients and health care providers seems to be focused primarily on modifying and configuring conventional PPs so they can transmit alerts or other information to wireless or other networks. Most PPs, however, must be located in close proximity to an IMD for alerts or other information to be transmitted to the PP. PPs also tend to be bulky, and uncomfortable to wear or position continuously over the IMD. Moreover, most PPs require extensive training for proper use, and as dedicated devices typically tied to one or more families of IMDs, usually become outmoded and outdated quickly due to the on-going rapid pace of computer hardware and software innovation.

To address the issues discussed above that are associated with conventional systems of communicating with IMDs, the present disclosure offers systems, devices and methods of communicating with an IMD using a portable electronic device and a mobile computing device (e.g., a smartphone or a tablet computer), which may obviate the need for dedicated clinician programmers or patient programmers, as discussed below in more detail.

FIG. 1 is a simplified block diagram of one embodiment of a medical system 20A according to various aspects of the present disclosure. The embodiment of system 20A shown in FIG. 1 includes an IMD 30. The IMD 30 can be implanted inside a patient's body. In the illustrated embodiment, the IMD 30 is an implantable pulse generator (IPG). The IPG is an example neurostimulator device, which may be battery-powered or battery-less devices that are designed to deliver electrical stimulation to a patient. Through proper electrical stimulation, the IPGs can provide pain relief for patients or restore bodily functions. One end of an example implanted lead 35 is coupled to the body of the IPG. The other end of the example implanted lead 35 includes multiple electrode surfaces 40 through which electrical current is applied to a desired part of a body tissue of a patient. The implanted lead 35 incorporates electrical conductors to provide a path for that current to travel to the body tissue from the IPG. Although only one implanted lead 35 is shown in FIG. 1, it is understood that a plurality of implanted leads may be attached to the IPG.

Although the IPG is used here as an example for the IMD 30, it is understood that the various aspects of the present disclosure apply to other IMDs as well. For example, an external pulse generator (EPG) may be employed in place of IMD 30, or IMD 30 may be a pacemaker, an implantable cardioverter-defibrillator, an implantable cardiac signal monitor, an implantable loop recorder, an implantable spinal cord stimulator, an implantable pelvic nerve stimulator, an implantable peripheral nerve stimulator, an implantable brain stimulator, a gastric system stimulator, and the like.

The system 20A also includes a mobile computing device 60. In the embodiment shown, the mobile computing device 60 is or comprises, by way of non-limiting example, a mobile smartphone such as an IPHONE®, an ANDROID® phone, a WINDOWS® phone, a BLACKBERRY® phone, or any other suitable smartphone. In other embodiments, the mobile computing device 60 is or may comprise a tablet computer (also referred to as a computer tablet), a notebook computer, or any other suitable computing device having a small or relatively small form factor. These may include an IPAD®, and ANDROID® tablet, a WINDOWS® tablet, or another suitable tablet. In yet other embodiments, the mobile computing device 60 is or may comprise a desktop computer or a laptop computer with a sophisticated operating system, for example a computer that is running a WINDOWS® operating system, a MAC® operating system, or a UNIX-based operating system. Such computers equipped with one or more of the sophisticated operating systems discussed above may be useful in contexts where remote controlling is needed, for example where the mobile computing device 60 needs to remotely control an external device. In some other embodiments, the mobile computing device 60 may comprise a simple web interface in addition to, or in place of, a comprehensive operating system. The mobile computing device 60 contains electronic circuitry and software implemented therein that enables communication with one or more external electronic devices under a suitable wired or wireless telecommunications protocol. The mobile computing device 60 also includes a screen 70 or another suitable visual or tactile communications interface. In the illustrated embodiment, the screen 70 is a touch-sensitive screen display and is configured to receive gesture-based user input (including touch input) and display an output to the user. The mobile computing device 60 may also include one or more physical or virtual buttons, for example a button 80, to facilitate a user's interaction with the screen 70. Various other aspects of the mobile computing device 60 will be discussed later in greater detail with reference to FIG. 16.

The embodiment of system 20A shown in FIG. 1 also includes a local server/router 85. The local server/router 85 is configured to conduct telecommunications with the mobile computing device 60, for example under the Wi-Fi protocol or a Bluetooth protocol. The local server/router 85 is also configured to communicate with a remote server 87 (or the Internet in general). Therefore, the mobile computing device 60 may also access the remote server 87 or the Internet either via the communications components built inside the mobile computing device 60, or may via the local server/router 85.

The system 20A further includes a portable electronic device 90. The portable electronic device 90 includes communications components therein configured to allow it to conduct telecommunications with the IMD 30, the mobile computing device 60, and/or the local server/router 85. In the embodiment illustrated in FIG. 1, the portable electronic device 90 may be a dongle-like device or a stick-like device. The portable electronic device 90 may include connectors 100 (which may be retractable) that are configured for connection with a power source, such as a household power outlet 110. In other words, in one embodiment the portable electronic device 90 may be plugged into the power outlet 110 to draw power from the power outlet 110. In other embodiments, the portable electronic device 90 may be electrically coupled to a power source through a charger (not illustrated herein). In yet other embodiments, the portable electronic device 90 may be powered by a battery. In these embodiments, the battery of the portable electronic device 90 can be used to charge the mobile computing device 60, in addition to providing power for its own circuitry. Portable electronic device may also be powered by one or more rechargeable batteries, which may or may not be configured for recharging through inductive means.

Figure 2:
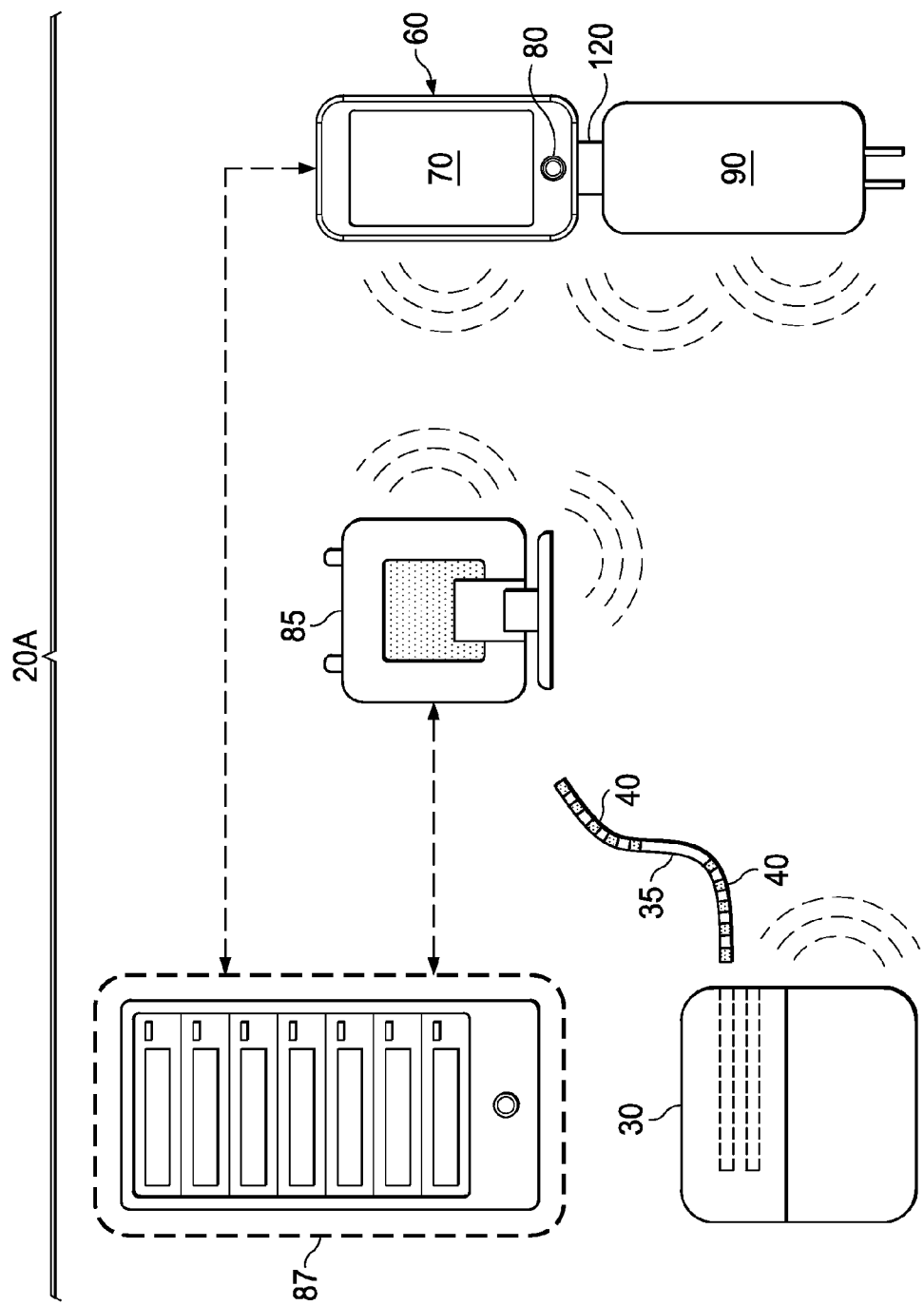

The portable electronic device 90 may also include a port 120 (or connector) that can be mated with a corresponding port or connector of an external electronic device. In various embodiments, the port 120 may include a USB port, a micro-USB port, an HDMI port, a Lightning® port, a Thunderbolt® port, or another suitable proprietary port. The port 120 enables the portable electronic device 90 to be physically attached to an external device such as the mobile computing device 60, for example in an embodiment shown in FIG. 2. Referring to FIG. 2, the portable electronic device 90 is physically attached to the mobile computing device 60 through the port 120. Electrical communication between the portable electronic device 90 and the mobile computing device 60 may be established via the port 120. Furthermore, in certain embodiments, the portable electronic device 90 may be used to provide power (i.e., charge) to the mobile computing device 60 through the connection established via the port 120.

Figure 3:
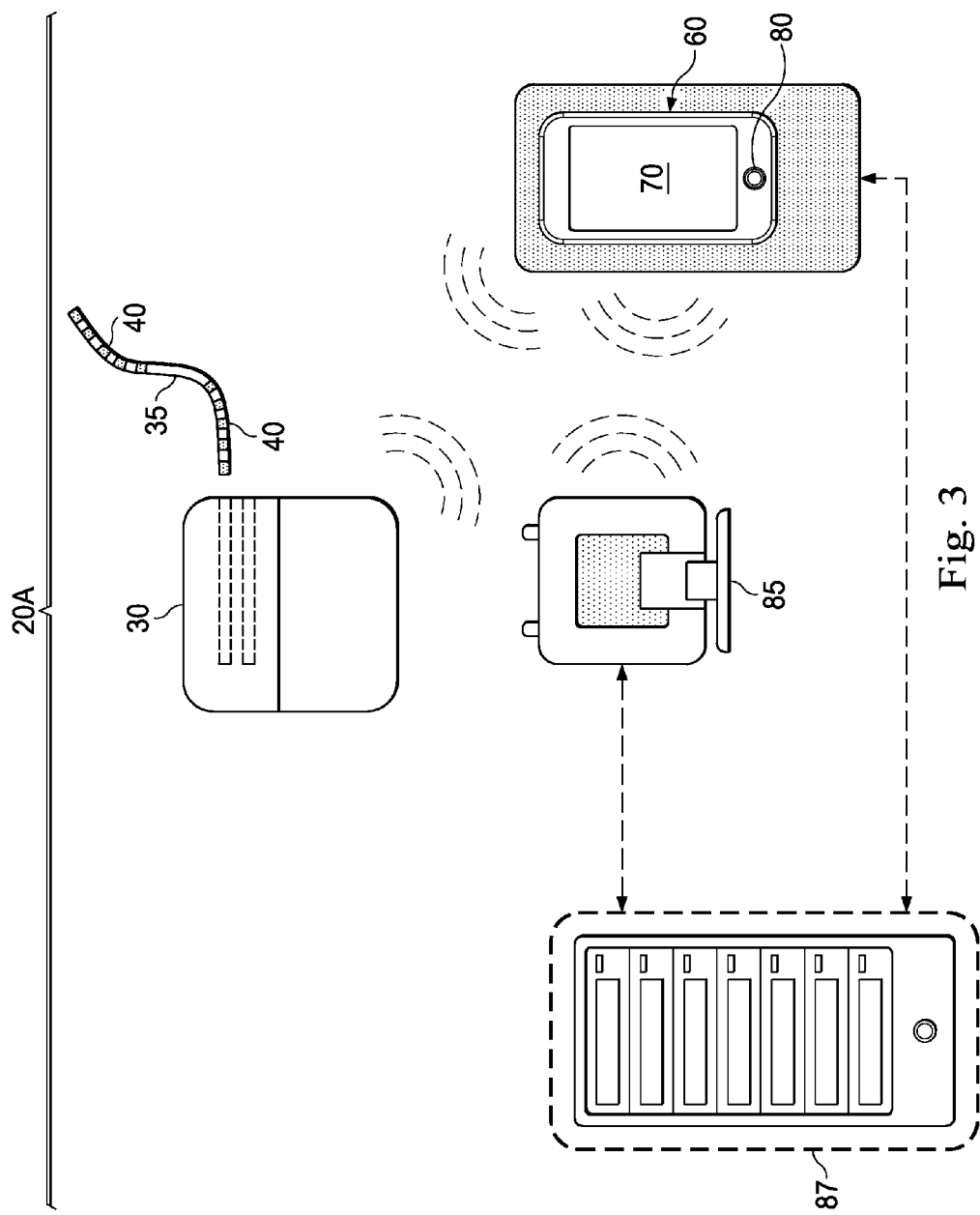

It is understood that the dongle-like or stick-like form factor shown in FIGS. 1-2 is merely one example form factor for the portable electronic device 90. Referring now to FIG. 3, a portable electronic device 90 in an alternative embodiment of the system 20A may have a case-like form factor, which is configured to encase or house the mobile computing device 60 therein. In addition to serving as a protector against drops, scratches, dust, etc., for the mobile computing device 60, the portable electronic device 90 may also provide additional power to the mobile computing device 60. For example, the battery of the portable electronic device 90 may be used to charge the electronic components of the mobile computing device 60 when the battery of the mobile computing device 60 depletes its charge. Other than the different form factors, the embodiment of the portable electronic device 90 shown in FIG. 3 may contain similar circuitry as the embodiment of the portable electronic device 90 shown in FIGS. 1-2. It is also understood that in other embodiments, the portable electronic device 90 may have any form factor that is suitable for easy portability. Portable electronic device 90 may also be configured as a patch or other device that is worn on or attached to a patient's body over IMD 30, thereby permitting enhanced communication coupling between IMD 30 and portable electronic device 90.

The portable electronic device 90 is configured to electrically or telecommunicatively couple the IMD 30 and the mobile computing device 60 together. For example, the portable electronic device 90 includes one or more communications components therein to conduct telecommunications with the IMD 30 under a first communications protocol and with the mobile computing device 60 under a second communications protocol different from the first communications protocol. In some embodiments, the first communications protocol includes a Medical Implant Communication Services (MICS) protocol, and the second communications protocol includes Wi-Fi, Bluetooth, DLNA, or any of the 3G or 4G cellular networking protocols. In other embodiments, the first and second communications protocol may each include a different wireless communications protocol or a wired communications protocol (i.e., with a hardware interface). Among other things, the first and second communications protocols may have different frequency bands and/or different modulation/demodulation techniques. As such, in some embodiments, the portable electronic device 90 may include a first communications component to carry out the communication with the IMD 30 under the first communications protocol, and it may include a separate second communications component to carry out the communication with the mobile computing device 60 under the second communications protocol.

In the embodiments shown in FIG. 1, the portable electronic device 90 communicates with the IMD 30 and the mobile computing device 60 wirelessly. However, the portable electronic device 90 may also communicate with the IMD 30 via the port 120, for example in the embodiment shown in FIG. 2. As discussed above, the port 120 allows the portable electronic device 90 to communicate with the mobile computing device via a hardware interface (or through a physical connection). In various example embodiments, the hardware interface may include, but is not limited to, an USB interface, a micro-USB interface, an HDMI interface, a Lightning® interface, a Thunderbolt® interface, or other proprietary hardware interfaces known in the art. In other words, the second communications protocol (under which the portable electronic device 90 communicates with the mobile computing device 60) need not be wirelessly-based, but that it could include a wired connection or a physical connection that involves attaching the portable electronic device 90 into a port of the mobile computing device 60, or vice versa.

One of the functionalities offered by the portable electronic device 90 involves its ability to serve as a "liaison" between the mobile computing device 60 and the IMD 30. In other words, the portable electronic device 90 allows the mobile computing device 60 to configure or program the IMD 30. Traditionally, a patient programmer (used by a patient) or a clinician programmer (used by a medical professional) is needed to communicate with the IMD 30, so that the IMD 30 can operate in a certain way. For example, in the case of an IPG as the IMD, the patient programmer may allow the patient to adjust the electrical stimulation provided by the IPG, such as by selecting a stimulation program, changing its amplitude, frequency, and other stimulation parameters, and by turning stimulation on and off.

Compared to the patient programmer, the clinician programmer is generally configured to allow its user to gain a much more advanced level of access to the IMD. In the case of the IPG as the IMD, the clinician programmer allows the medical professional to configure the IPG (or other system components) in manners not permitted for the patient or by the patient programmer. For example, the clinician programmer can set up a plurality of stimulation programs from among which the patient may choose, select the active set of electrode surfaces in a given stimulation program, and/or pre-set upper and lower limits for the patient's adjustments of amplitude, frequency, and other parameters (for safety reasons).

Although patient programmers and clinician programmers are useful and versatile devices, they are generally expensive and may be limited in the types of communication functions they are capable of performing. Another drawback associated with the traditional patient/clinician programmers is that they are required to undergo an extensive (and often times long) FDA approval process. Each type of programmer may need to be qualified in conjunction with the specific type of medical device it is intended to control. The FDA approval process further increases costs associated with traditional patient/clinician programmers. In addition, and as described above, clinician programmers are typically designed and configured to serve one or more families of IMDs, and are intended to have a relatively long field life. Together with regulatory hurdles, these factors often result in clinician programmers becoming rather long in the tooth from a technical perspective only a short time after they have been introduced to the market. Consequently, clinician programmers typically become technical dinosaurs shortly after commercialization.

According to the various aspects of the present disclosure, the mobile computing device 60 in combination with the portable electronic device 90 collectively provide an effective replacement for traditional patient programmers and clinician programmers. In some embodiments, the mobile computing device 60 and/or the portable electronic device 90 may be configured to run a software application that when executed, provides a user interface on the screen 70 that mimics a user interface of a traditional clinician programmer. In other embodiments, the mobile computing device 60 and/or the portable electronic device 90 may be configured to run a software application that when executed provides a user interface on the screen 70 that mimics a user interface of a traditional patient programmer. In still other embodiments, the mobile computing device 60 and/or the portable electronic device 90 may be configured to run software applications that when executed provide a user interface on the screen 70 that mimics a user interface of a traditional patient programmer or a traditional clinician programmer, according to the software application that is being executed. In further embodiments, the mobile computing device 60 and/or the portable electronic device 90 may be configured to run software applications that are executed to provide a user interface on the screen 70 that mimics a user interface of a traditional patient programmer or a traditional clinician programmer, according to the software application that is being executed, and further according to user authorization levels that are associated with the user and the software application(s) that is/are to be executed. More about such embodiments is said below.

In some embodiments, such software applications may be provided by a manufacturer of the IMD or a manufacturer of the patient/clinician programmer. For example, the maker of the software application may offer an application for download and installation via an "app-store". The selected or authorized software application may be downloaded by a user of the mobile computing device 60 through the "app-store". Thereafter, the software application may reside on a local memory of the mobile computing device 60 or on a remote "cloud" server (not illustrated herein) communicatively coupled to the mobile computing device 60.

Software applications may be executed in response to a user's engagement with the mobile computing device 60, for example via a touch input to the screen 70. In other embodiments, software applications may be pre-installed on the portable electronic device 90 or on the IMD 30. In such embodiments, software applications may be invoked remotely by an appropriate user engagement via the mobile computing device 60, and the information for displaying the user interface mimicking the patient/clinician programmer may be transmitted (or at least in part transmitted) to the mobile computing device 60, so that the user interface can be displayed on the screen 70 of the mobile computing device 60.

In some embodiments, the portable electronic device 90 may be configured to update its own firmware/software (since it has the ability to access the Internet), or even the firmware/software of the IMD 30 via network connections.

This provides convenience for the patient, since the patient no longer needs to come to a doctor's office just to receive a firmware/software update or upgrade. For example, suppose a firmware/software update is developed to fix a bug in the portable electronic device 90, or in the IMD 30, or in the software for mimicking the patient/clinician programmers, or if the firmware/software update is developed to add new features to these devices. Once the developers for the firmware/software update verifies that such update works, the update can be pushed out to the portable electronic device 90 through the appropriate network connections to the portable electronic device 90, and if needed, the portable electronic device 90 may push the update to the IMD 30 or the mobile computing device 60.

In certain embodiments, the software application being executed by the portable electronic device 90 or the IMD 30 may be "telecast" onto the screen 70 of the mobile computing device 60 the graphics that mimic the patient/clinician programmer user interfaces. This may be done via the (wireless or wired) telecommunications conducted under the first and second communications protocols discussed above. Stated differently, the graphical data for displaying the patient/clinician programmer user interfaces is generated on the portable electronic device 90 or on the IMD 30 and is transmitted in real time to the mobile computing device 60.

Regardless of the particular approach employed to implement and/or execute the software application, the user's (be it a patient or a medical professional) commands are received through the user interface and are sent to the IMD 30 through the portable electronic device 90. For example, the user's commands may be modulated in a format suitable for transmission under the second communications protocol (e.g., Wi-Fi, Bluetooth, Cellular, or hardware interface). The modulated data is then sent to the portable electronic device via communications conducted between the mobile computing device 60 and the portable electronic device 90 under the second communications protocol.

The portable electronic device 90 may then demodulate the received data and re-modulate it in a format suitable for transmission under the first communications protocol (e.g., MICS). The re-modulated data is then sent (by the portable electronic device 90) to the IMD 30 via communications conducted between the portable electronic device 90 and the IMD 30 under the first communications protocol. The IMD 30 may then demodulate the received data to receive the user commands and is configured by the commands accordingly. Similarly, the IMD 30 may transmit data back to the mobile computing device 60 via the portable electronic device 90.

The system 20A discussed above provides numerous advantageous over traditional systems where a dedicated patient programmer or clinician programmer is used to interact with the IMD 30. However, it is understood that not all advantages are necessarily discussed herein, other embodiments of the system 20A may offer different advantages, and that no particular advantage is required for all embodiments.

One advantage is that the system 20A has reduced costs compared to traditional medical systems. The expensive patient programmer or clinician programmer can be effectively replaced by the mobile computing device 60 and the portable electronic device 90. Often times, the user would already own the mobile computing device 60 for his/her personal use. Therefore, the mobile computing device 60 does not add extra costs to the system 20A. In addition, the portable electronic device 90 is cheaper to produce than the traditional patient/clinician programmers. First, the portable electronic device 90 does not necessarily require a screen or other types of user input/output mechanism. Second, the portable electronic device 90 does not require hardware as advanced or sophisticated as that on a patient programmer or a clinician programmer, since some of the computing tasks may be delegated to the mobile computing device 60 in various embodiments. In other words, the system 20A can leverage the mobile computing device 60's advanced processing power, large memory storage, and intuitive communications interface (e.g., a touch-sensitive graphical user interface displayed on the screen 70), instead of trying to duplicate it in an expensive patient/clinician programmer. Third, the portable electronic device 90 does not need to undergo as rigorous of an FDA approval process as a patient programmer or a clinician programmer, since it is a much simpler device. The potentially quicker FDA approval process also leads to cost savings. In addition, and according to some embodiments, system 20A can also be configured for use in countries where FDA approval or TuV/CE Mark approval is not required, and where changes in software and functionality can therefore be implemented in the field with users much more quickly than would otherwise be the case.

Another advantage is that the system 20A offers more convenience and familiarity to an average user, especially users who are patients. With traditional systems using the dedicated patient/clinician programmers, the end user—be it a patient or a medical professional—would have to carry the patient programmer or the clinician programmer around. Though these devices are designed with portability in mind, they may still be cumbersome to carry. In the case of clinician programmers, they may be too large to fit into a pocket. In addition, the user would have to provide maintenance for the patient/clinician programmer, for example by charging it periodically.

In comparison, the system 20A herein obviates the need for carrying an extra device, as most users already have their own mobile computing device (e.g., smartphone or tablet). In other words, the user need not carry an extra device, since he/she merely carries a single mobile computing device 60 instead of a dedicated patient/clinician programmer in addition to the mobile computing device. The portable electronic device 90 need not necessarily be carried by the user at all times either. For example, it could be plugged into the power outlet 110 and remain plugged in, as long as the user is at home or in an office. In other embodiments, such as the embodiments shown in FIGS. 2 and 3, the portable electronic device 90 may also be attached (FIG. 2) to the mobile computing device 60, or serve as a protective case (FIG. 3) for the mobile computing device 60. In these embodiments, the portable electronic device 90 and the mobile computing device 60 appear as a single device from the user's perspective.

Maintenance is also easier, since the user need not maintain (e.g., charge) the dedicated patient/clinician programmer. They may charge the mobile computing device and the portable electronic device together. Furthermore, most users who own an mobile computing device are familiar with its operations and functionalities, and thus they may feel more comfortable using the mobile computing device 60 to program or configure the IMD 30, even if the user interface (used for the configuration or programming of the IMD 30) may be substantially similar to the user interface on a dedicated patient/clinician programmer.

Yet another advantage offered by the system 20A is that the mobile computing device 60 can be easily replaced. In traditional systems, if a dedicated patient programmer or clinician programmer becomes damaged or otherwise defective, a replacement unit may or may not be readily available.

It may take a relatively long period of time before the user can obtain a replacement unit. This is inconvenient for the user. In comparison, the mobile computing device 60 can be easily and with much lower cost be replaced if it becomes defective, or even if the user just wants to get a different type of mobile computing device. The new mobile computing device can interact with the IMD 30 via the portable electronic device 90 in the same manner as the previous (i.e., replaced) mobile computing device, thereby offering the user a seamless transition.

Along the same lines, the user may also be allowed to use two or more different mobile computing devices 30 (though not necessarily at the same time) to interact with the IMD 30, since each of the mobile computing devices is capable of performing the configuration or programming of the IMD 30. For example, the portable electronic device 90 may function as a de facto router to allow multiple mobile computing devices to communicate with multiple IMDs. In some embodiments, the mobile computing devices may have a one-to-one correspondence with the IMDs (e.g., each mobile computing device communicates with a designated IMD through the portable electronic device 90). In other embodiments, each mobile computing device may communicate with a plurality of IMDs through the portable electronic device. In yet other embodiments, a plurality of mobile computing devices may communicate with the same IMD through the portable electronic device (though not at the same time). In these above embodiments, the portable electronic device 90 may include electrical circuitry and/or software and firmware that allow it to have multiplexing capabilities. For example, the portable electronic device 90 may include one or more multiplexors and/or demultiplexers, as well as a plurality of antennas (e.g., a plurality of MICS antennas). Again, the ability to use multiple "programming devices" (i.e., the mobile computing devices) offers the user greater flexibility and convenience. It is understood that other embodiments of the system 20A may offer additional advantages, which will be discussed below in association with their embodiments.

According to the various aspects of the present disclosure, the mobile computing device 60 is configured to display different user interfaces in response to different users being authenticated. These different user interfaces will also have different levels of access to the IMD 30. For example, if a patient user is authenticated, the mobile computing device 60 may display a first user interface that is similar to a user interface on a conventional patient programmer. The first user interface only allows the patient user to gain a basic level of access to the IMD 30, such as turning stimulation on or off, toggling between different predefined stimulation programs, or adjusting one or more stimulation parameters such as increasing or decreasing stimulation current amplitude.

On the other hand, if a medical professional user is authenticated, the mobile computing device 60 may display a second user interface that is similar to a user interface on a conventional clinician programmer. The second user interface allows the medical professional user to gain an advanced level of access to the IMD 30, such as selecting target medical devices for programming from a plurality of available medical devices, configuring the stimulation programs, defining pain maps or stimulation maps, entering patient data, etc. These aspects of the present disclosure are discussed below in greater detail with reference to FIGS. 4-13.

Figure 4:
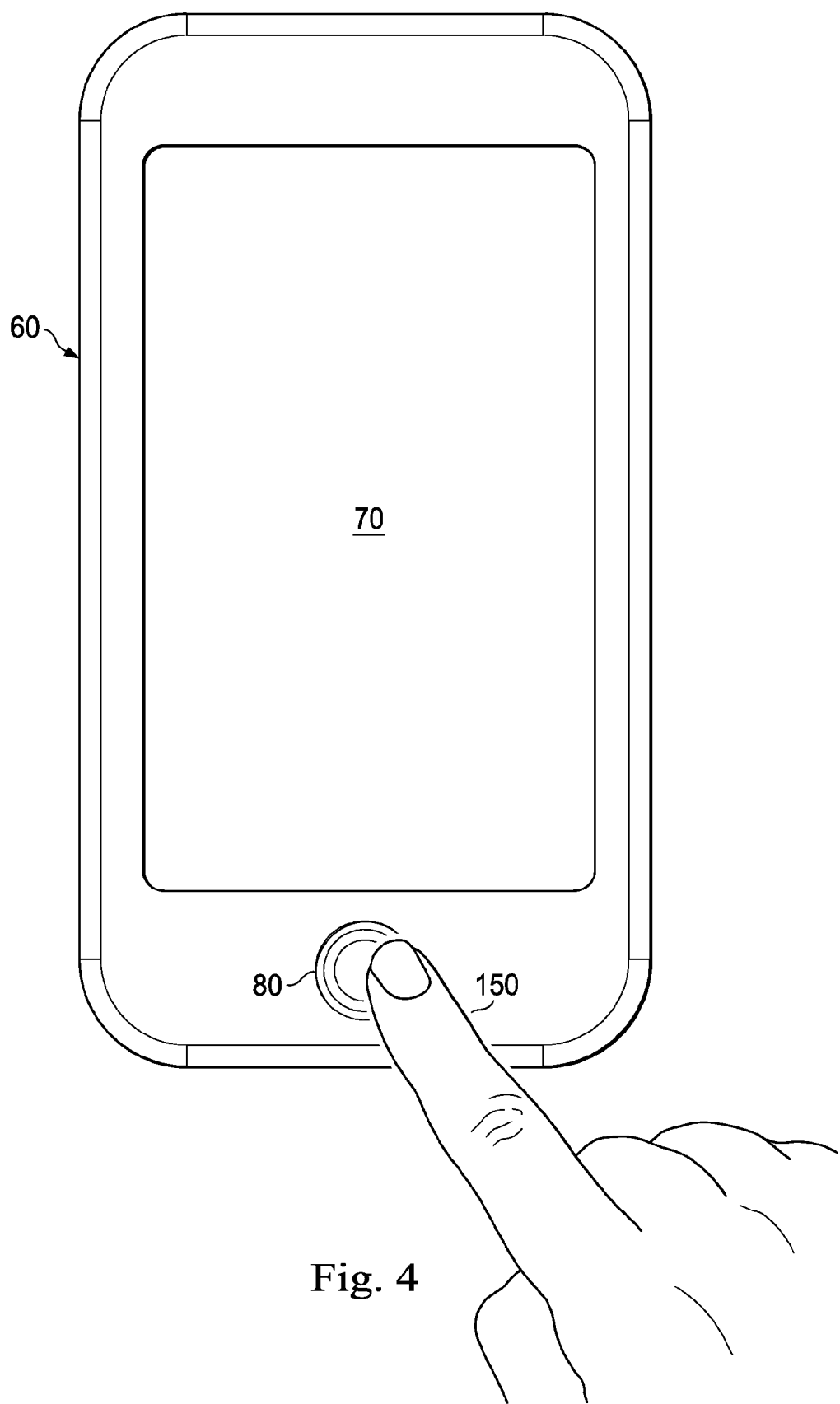
FIGS. 4-7, 8A-8B, 9, 10A-10B, and 11-13 illustrate an example mobile computing device that is a part of the medical systems of FIGS. 1-3 and 14-15 as well as the various portions of user interfaces displayed on a screen of the mobile computing device according to various embodiments of the present disclosure.

Referring now to FIG. 4, the mobile computing device 60 is configured to authenticate a user based on the user's biometric data. In the illustrated embodiment, the biometric data is the user's fingerprint, which may be "read" or captured by a suitable mechanism on the mobile computing device 60, such as the button 80. In other embodiments, the biometric data may include the user's voice or eye composition (e.g., retina), etc. At some time before the authentication step illustrated in FIG. 4 takes place, the user supplies his/her biometric data to the mobile computing device 60.

For example, the user may have already "registered" a fingerprint of one of his/her fingers 150 with the mobile computing device 60 at a registration stage earlier. Other users may also be allowed to register their biometric data (e.g., their fingerprints or retinal scans) with the mobile computing device 60. Now, suppose the user wishes to authenticate himself/herself, he/she may scan the finger 150 by touching and holding the button 80, or via some other suitable scanning mechanism such as a camera or a sensor. If the scanned fingerprint matches one of the pre-registered fingerprints, the user unlocks the mobile computing device 60.

Figure 5:
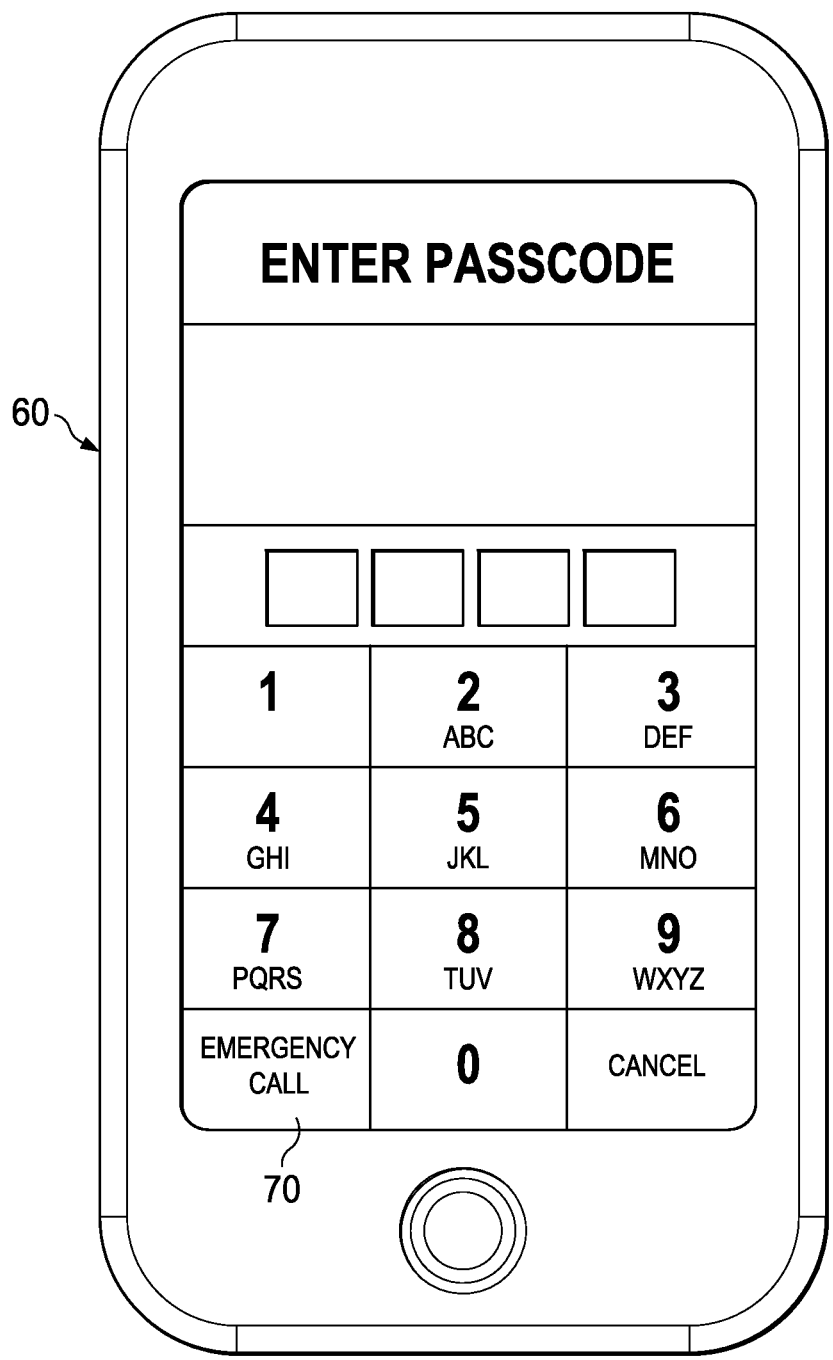

Referring now to FIG. 5, the mobile computing device 60 may also authenticate the user via a passcode or password. As illustrated, the mobile computing device 60 may display an image the screen 70 that prompts the user to enter the passcode. The passcode may be based on numbers, letters, or both. Again, different authorized users may have registered their own respective passcodes with the mobile computing device 60 previously. Each of the authorized users may have his/her own passcode. Once the user supplies a correct passcode, the mobile computing device 60 will unlock itself. In some embodiments, the mobile computing device 60 may employ a combination of the biometric authentication described with reference to FIG. 4 and the passcode authentication described with reference to FIG. 5 in order to authenticate the user.

It is understood that the authentication process discussed above may also be performed at least in part via the portable electronic device 90 or by the remote server 87. For example, as a part of the registration process, the portable electronic device 90 and/or the remote server 87 may also store the different users' biometric data or their respective passcodes. When a user undergoes authentication later, the biometric data or passcode supplied by that user may be forwarded by the mobile computing device to the portable electronic device 90 and/or to the remote server 87, which will compare the supplied biometric data and/or passcode with those on file (e.g., stored electronically therein). If there is a match, the portable electronic device 90 or the remote server 87 will then instruct the mobile computing device 60 to grant access to the user, along with the appropriate privileges that user should have in terms of accessing the IMD 30. Otherwise, access to the mobile computing device 60 will be denied.

Furthermore, in some other embodiments, the portable electronic device 90 may include a biometric data scanner or an input/output user interface, so that the user may supply his/her biometric data and/or the passcode directly to the portable electronic device 90 (rather than through the mobile computing device 60).

Figure 6:
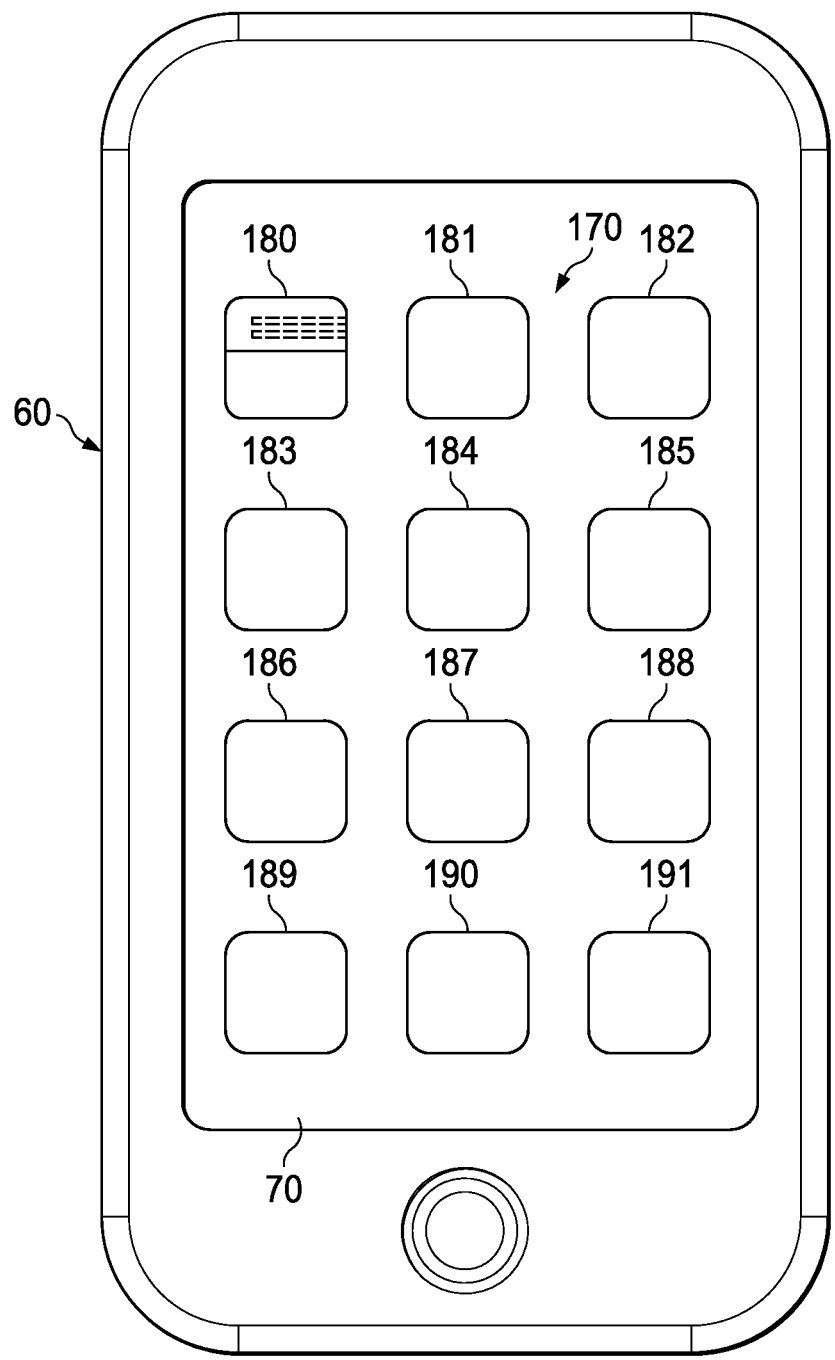

Referring now to FIG. 6, once the user is authenticated (by the mobile computing device 60, or by the portable electronic device 90, or by the remoter server 87, or combinations thereof), a home screen 170 may be displayed on the screen 70. In the illustrated embodiment, the home screen 170 may include a plurality of icons 180-191. These icons 180-191 may correspond to different applications that can be executed by the mobile computing device 60. In particular, the icon 180 corresponds to the application that can be executed to allow the mobile computing device 60 to configure the IMD 30.

For example, if the user touches the icon 180 (or engages it in another suitable manner), it will trigger a display of an appropriate user interface for configuring the IMD 30, since the mobile computing device 60 already "knows" the user's identity based on the previous authentication step discussed above with reference to FIGS. 4-5. Stated differently, the application triggered by pressing the icon 180 will display a specific user interface based on that user's identity. In this manner, the engagement of the icon 180 by different users will trigger the display of different user interfaces (with different levels of access) for configuring the IMD 30.

Figure 7:
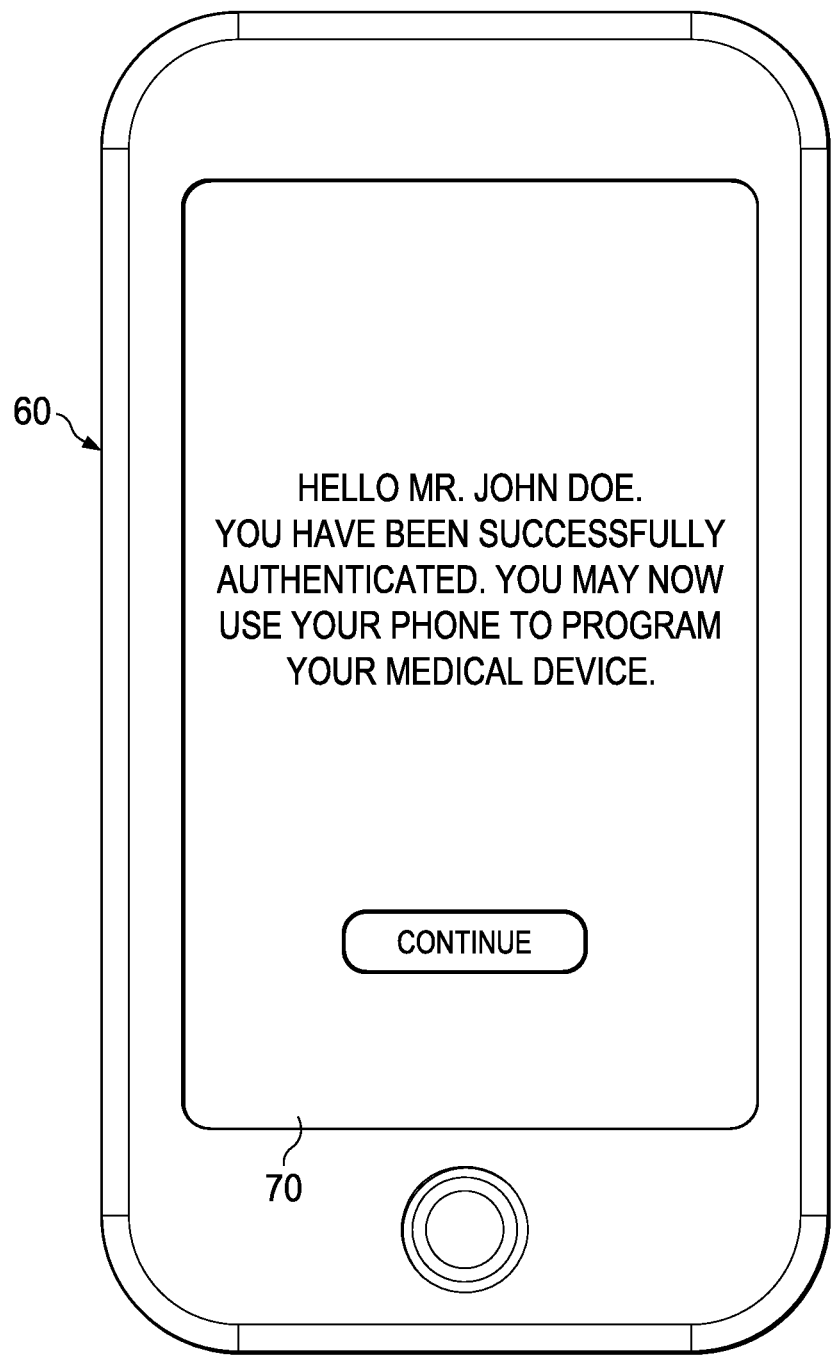
Figure 8A:
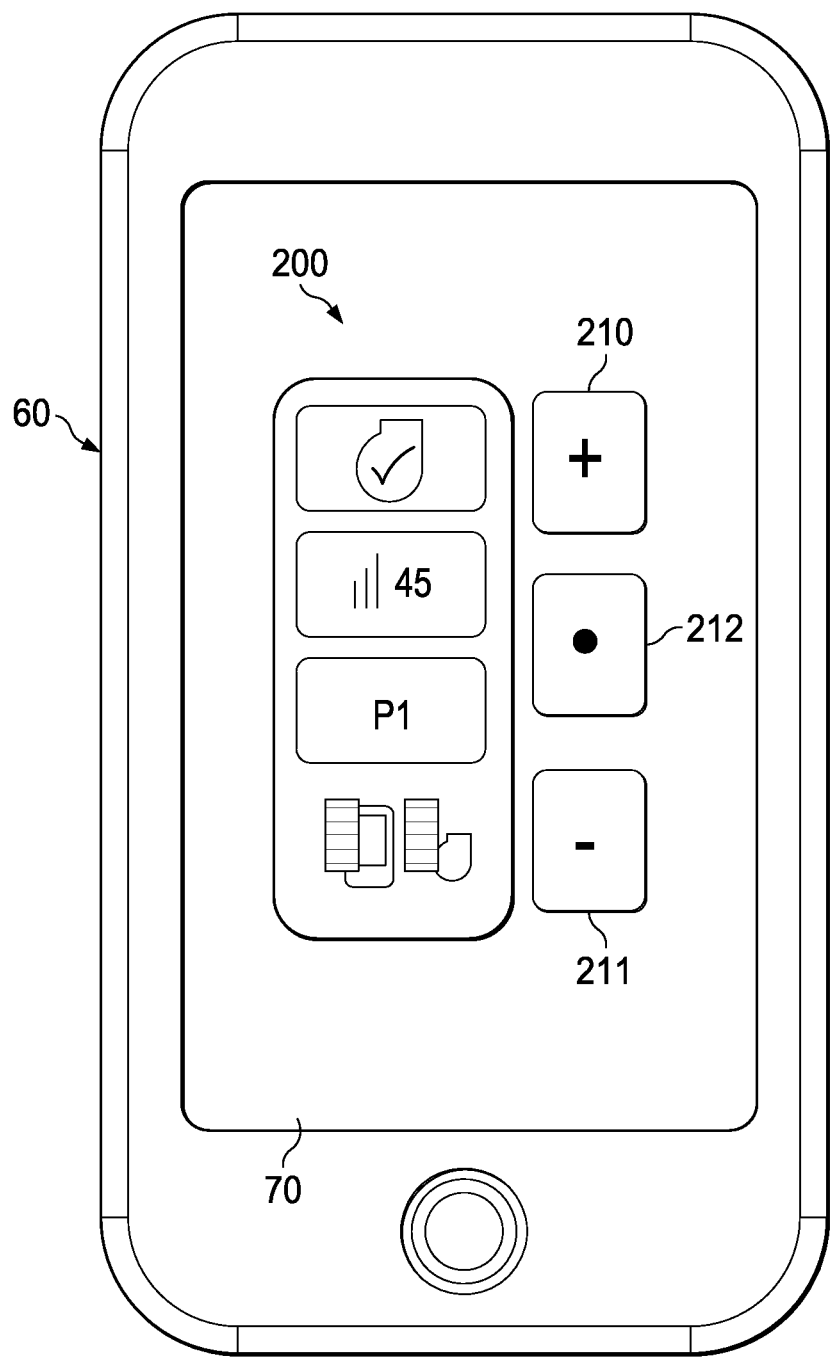
Figure 8B:
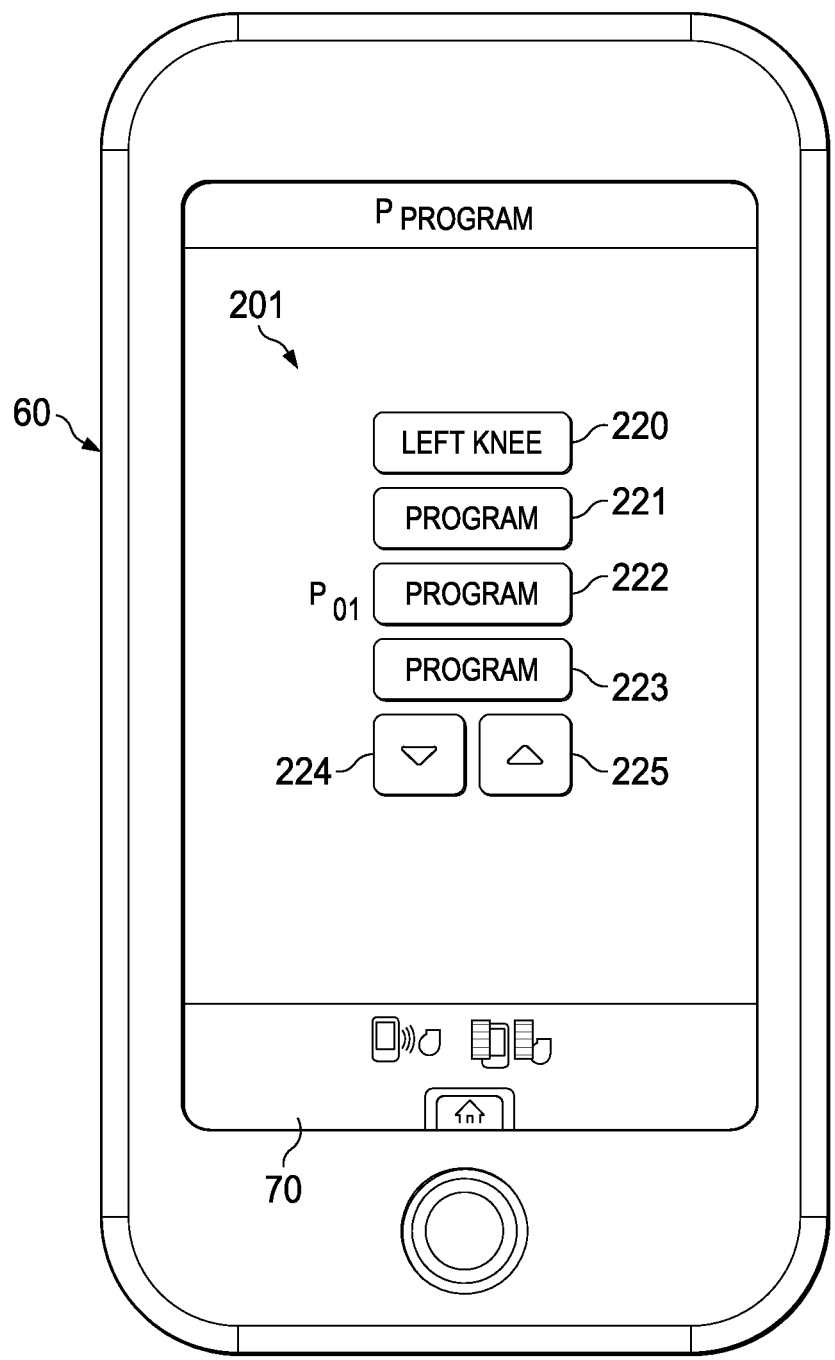

For example, referring now to FIGS. 7 and 8A-8B, if the user is a patient inside whom the IMD 30 is implanted, the patient user's engagement of the icon 180 will trigger the display (on the screen 70) of a user interface that mimics that of a patient programmer. As shown in FIG. 7, the mimicked patient programmer interface may first display a greetings screen to let the user know that the authentication of the patient is successful. For example, if the patient user's name is John Doe, the greetings screen may read, "Hello Mr. John Doe. You have been successfully authenticated. You may now use your phone to program your medical device." The greetings screen gives confirmation to the user that the mobile computing device has recognized him/her as the authorized patient user. The user may now proceed with the programming with the IMD as shown in FIGS. 8A-8B.

As discussed above, for the patient's safety and convenience, the patient programmer user interface is typically arranged to allow limited or basic access to the IMD 30. In this manner, the patient user need not learn (and possibly be confused) by the numerous programming features available for configuring the IMD, or risk an inadvertent programming mistake that could lead to undesirable operation of the IMD 30 (e.g., excessive stimulation, or stimulation in an incorrect region).

FIGS. 8A-8B illustrate different examples of patient programmer user interfaces 200-201. The user interface 200 in FIG. 8A allows the patient user to increase or decrease stimulation current amplitude via virtual buttons 210-211, or turn on and off stimulation via a virtual button 212. The user interface 201 in FIG. 8B allows the patient user to toggle between a plurality of pre-defined stimulation programs 220-223 via virtual button 224-225. The user interfaces 200-201 may also display other basic information such as the battery charge or the signal strength of the IMD 30. Of course, it is understood that these patient programmer user interfaces 200-201 are merely examples, and that other suitable types of patient programmer interfaces may be displayed by the mobile computing device 60 in response to the authentication of a patient user.

Figure 9:
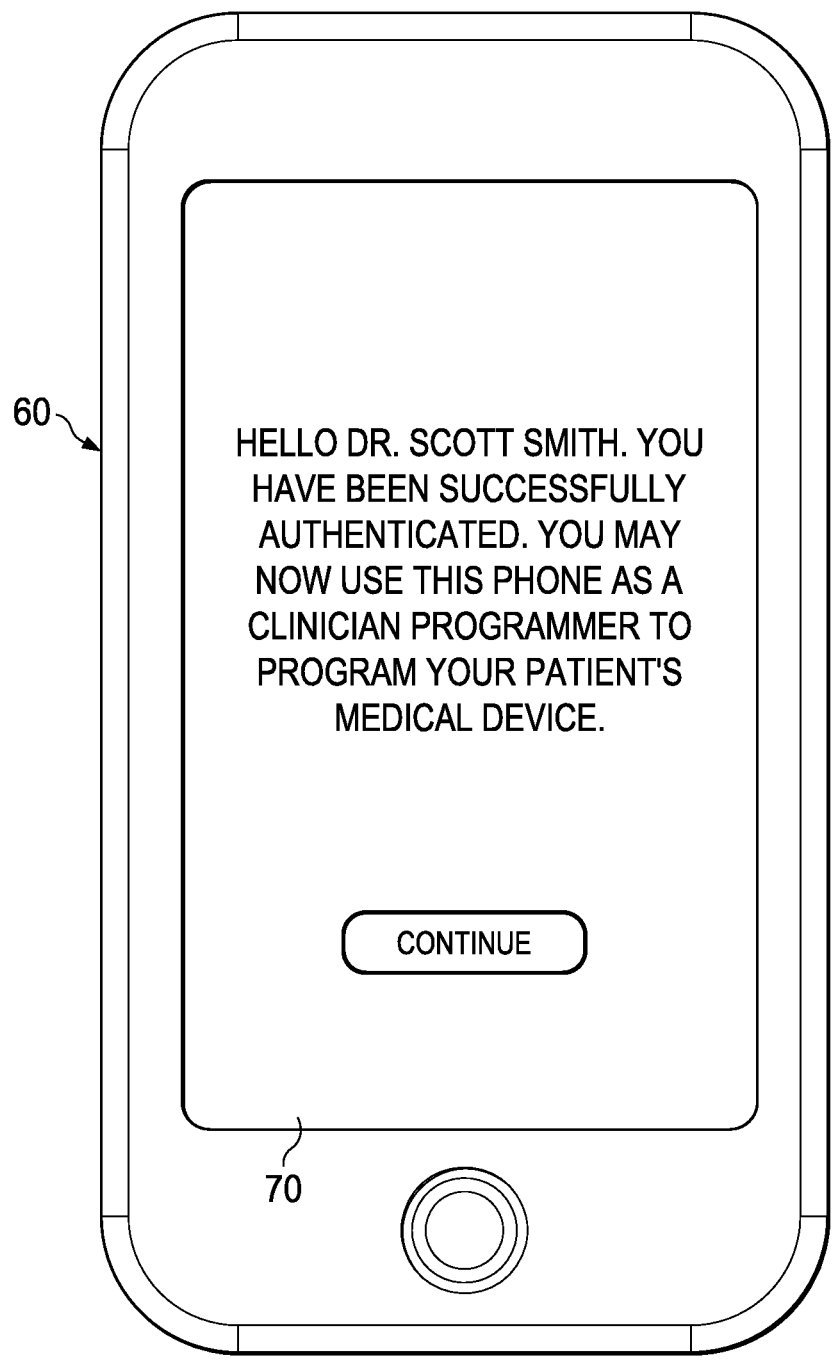
Figure 10A:
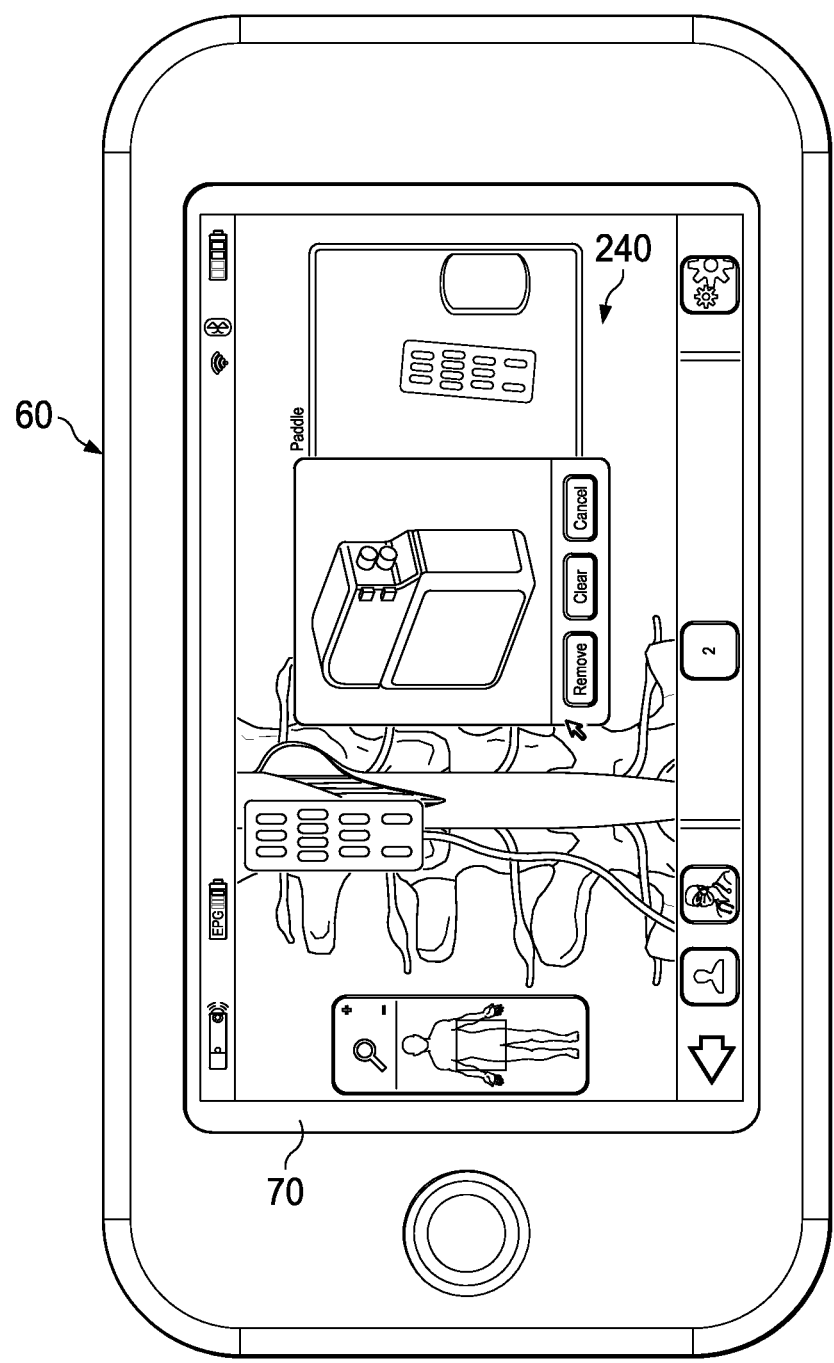
Figure 10B:
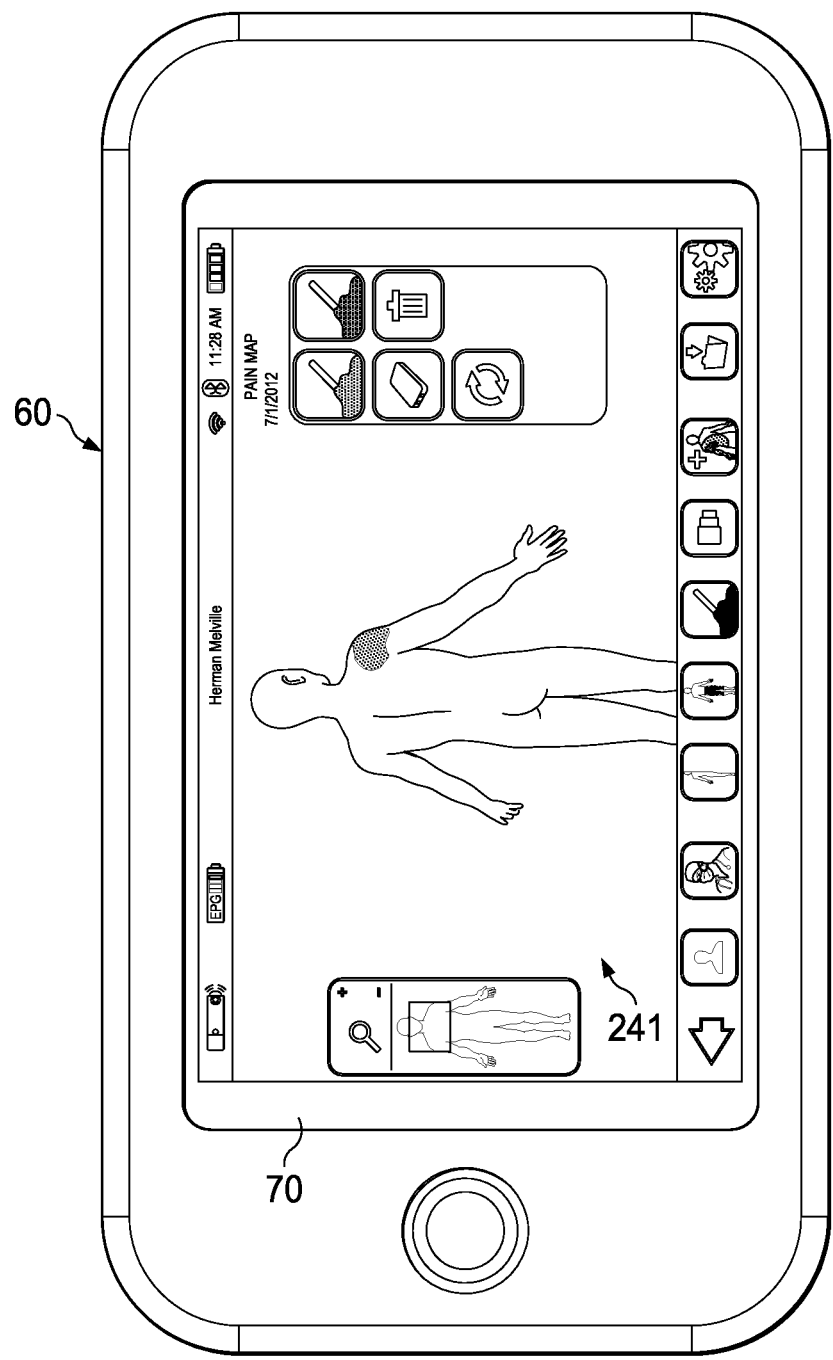

Referring now to FIGS. 9 and 10A-10B, if the user is a medical professional who is supposed to treat the patient, the medical professional user's engagement of the icon 180 will trigger the display (on the screen 70) of a user interface that mimics that of a clinician programmer. As shown in FIG. 9, the mimicked clinician programmer interface may first display a greetings screen to let the user know that the authentication of the medical professional is successful. For example, if the medical professional's name is Scott Smith, the greetings screen may read, "Hello Dr. Scott Smith. You have been successfully authenticated. You may now use this phone as a clinician programmer to program your patient's medical device." The greetings screen gives confirmation to the medical professional that the mobile computing device 60 has recognized him/her as the authorized medical professional user. The medical professional may now proceed with the programming of the IMD as shown in FIGS. 10A-10B.

As discussed above, the clinician programmer user interface is typically arranged to allow advanced access to the IMD 30. This is because the medical professional may need to have full access to the IMD 30 in order to develop an effective treatment plan or program for the patient.

FIGS. 10A-10B illustrate different examples of clinician programmer user interfaces 240-241. The user interface 240 in FIG. 10A allows the medical professional user to select an IMD from a plurality of available medical devices and position the selected IMD in a target anatomical environment of the patient's body. The user interface 241 in FIG. 10B allows the medical professional user (sometimes with the patient's help) to draw pain maps or stimulation maps on a human body model representing the patient's body. Though not illustrated, the clinician programmer user interface may also allow the medical professional user to create and edit patient records, define stimulation programs and/or program sets, generate reports, set safety controls, make diagnoses, etc. Various aspects of an example clinician programmer user interface are discussed in more detail in U.S. patent application Ser. No. 13/601,631, filed on Aug. 31, 2012, and entitled "Programming and Virtual Reality Representation of Stimulation Parameter Groups" to Norbert Kaula, et al., and in U.S. patent application Ser. No. 13/601,504, filed on Aug. 31, 2012, and entitled "Touch Screen Safety Controls for Clinician Programmer" to Norbert Kaula, et al., and in U.S. patent application Ser. No. 13/601,631, filed on Aug. 31, 2012, and entitled "Programming and Virtual Reality Representation of Stimulation Parameter Groups" to Norbert Kaula, et al., and in U.S. patent application Ser. No. 13/973,219, filed on Aug. 22, 2013, and entitled "Creating Two Dimensional Representations of a Three Dimensional Pain Map for Display and Printing" to Norbert Kaula, et al., and in provisional U.S. Patent Application No. 61/824,296, filed on May 16, 2013, entitled "Features and Functionalities of an Advanced Clinician Programmer," to Norbert Kaula, et al., the content of each of which is hereby incorporated by reference in its respective entirety.

Of course, it is understood that these clinician programmer user interfaces 240-241 as well as those discussed in the various patent applications incorporated by reference herein are merely examples, and that other suitable types of patient programmer interfaces may be displayed by the mobile computing device 60 in response to the authentication of a medical professional user.

In embodiments where the size of the screen 70 of the mobile computing device 60 is small (e.g., when the mobile computing device 60 is a smartphone), the mobile computing device 60 may telecommunicatively "cast" or "project" the user interfaces discussed above may onto an external display. The external display may include a computer monitor, a television set, or a tablet computer, which may all have a larger screen than a smartphone. The larger screen of these devices allows the user interfaces to be better and more accurately viewed. In some embodiments, the user interfaces may be displayed on the mobile computing device 60 and an external device simultaneously, for example in accordance with U.S. patent application Ser. No. 13/600,875, filed on Aug. 31, 2012, entitled "Clinician Programming System and Method", the disclosure of which is hereby incorporated by reference in its entirety. As such, two or more people (e.g., the patient and his/her healthcare provider) are able to view the same user interface at the same time.

Based on the above descriptions, it can be seen that one aspect of the present disclosure involves automatically displaying a suitable user interface for any one of a plurality of users in response to that specific user's identity. For example, if a user A has been authenticated as a patient, the mobile computing device 60 automatically displays a patient programmer user interface that is suitable for that patient, where the patient programmer user interface has only basic levels of access to the IMD 30. On the other hand, if a user B has been authenticated as a medical professional, the mobile computing device 60 automatically displays a clinician programmer user interface that is suitable for the medical professional, where the clinician programmer user interface is not only visually different from the patient programmer user interface, but it also has a more advanced level of access to the IMD 30 compared to the patient programmer user interface.

By allowing different types of user interfaces to be displayed on the same mobile computing device 60, the present disclosure offers versatility, simplicity, and flexibility compared to traditional systems where separate dedicated patient programmers and clinician programmers are needed for different users to interact differently with an IMD.

Figure 11:
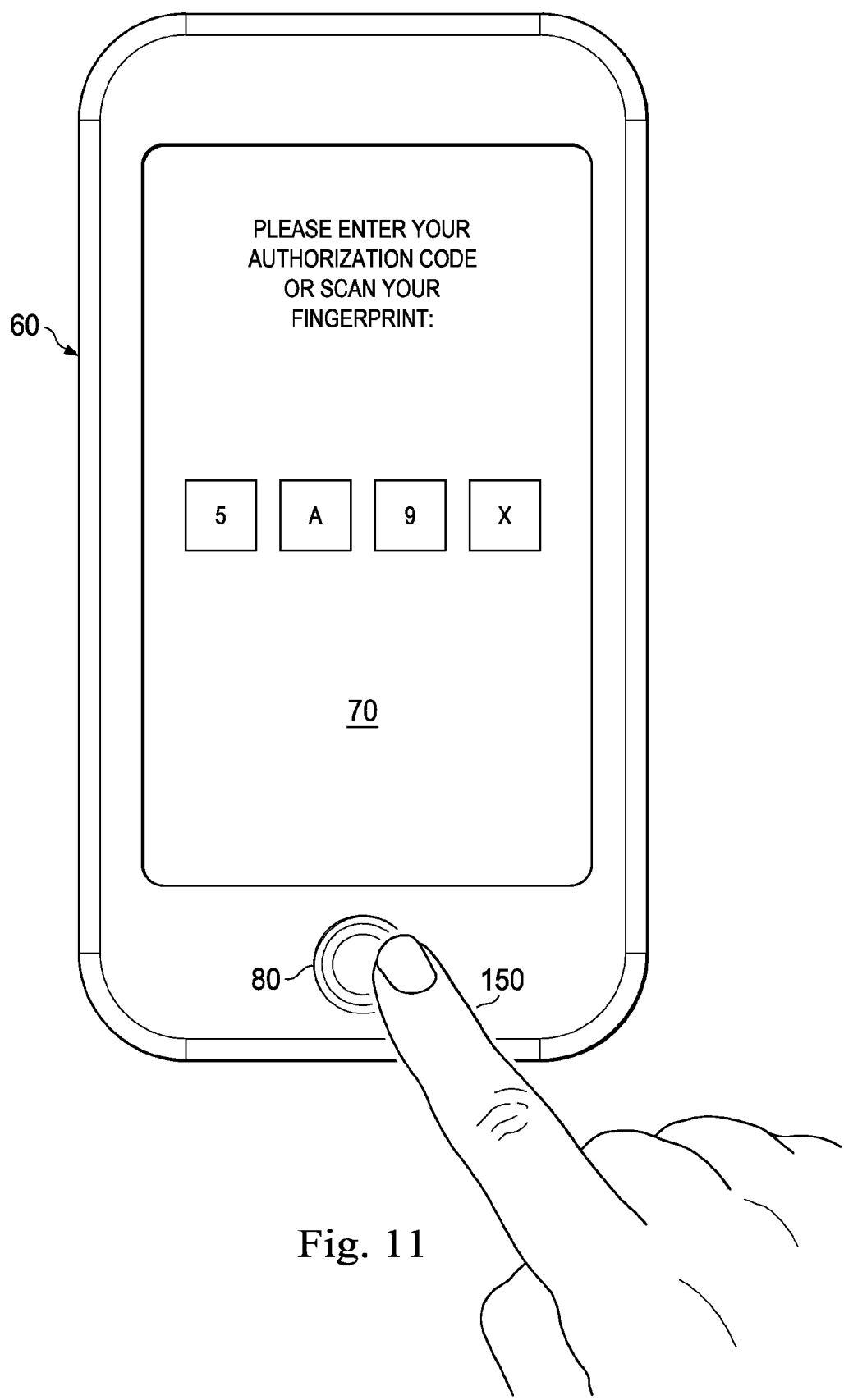

In some alternative embodiments, the engagement of the icon 180 alone will not necessarily trigger the display of the different user interfaces discussed above. Instead, the user may be asked to complete another step of verification before the target user interface is displayed. For example, after the icon 180 is engaged to execute the software application for mimicking the patient/clinician programmer interface, the user may be asked to input another authorization code as shown in FIG. 11. The authorization code may be a combination of a plurality of alphanumeric characters in some embodiments, but may also include a biometric scan in some other embodiments. Different users have different authorization codes (or different biometric scan data). Therefore, a patient user may have a first authorization code that will allow the patient programmer user interface (e.g., shown in FIGS. 7 and 8A-8B) to be displayed, while a medical professional user may have a second authorization code (different from the first authorization code) that will allow the clinician programmer user interface (e.g., shown in FIGS. 9 and 10A-10B) to be displayed.

In some embodiments, the verification step shown in FIG. 11 may be incorporated to provide an additional level of security in addition to the biometric-based or passcode-based authentication discussed above. In other embodiments, the verification step shown in FIG. 11 may be used in place of the biometric-based or passcode-based authentication discussed above. In further embodiments, various types of device IDs may be used instead. The device IDs may include, but are not limited to, Media Access Control (MAC) addresses, Mobile Equipment Identifiers (MEIDs), Electronic Serial Numbers (ESNs), International Mobile Station Equipment Identity (IMEIs), product numbers, serial numbers, or Ethernet addresses. In yet other embodiments, the verification step shown in FIG. 11 may be omitted altogether.

Although a patient programmer user interface and a clinician programmer interface have been used to illustrate some of the concepts of the present disclosure, it is understood that the present disclosure is not limited to only these two different types of user interfaces with their respective levels of access to the IMD. In fact, the mobile computing device 60 is configured to automatically display a plurality of other user interfaces (different from either the patient programmer interface or the clinician programmer interface) each with its own level of access to the IMD 30, as discussed below.

Figure 12:
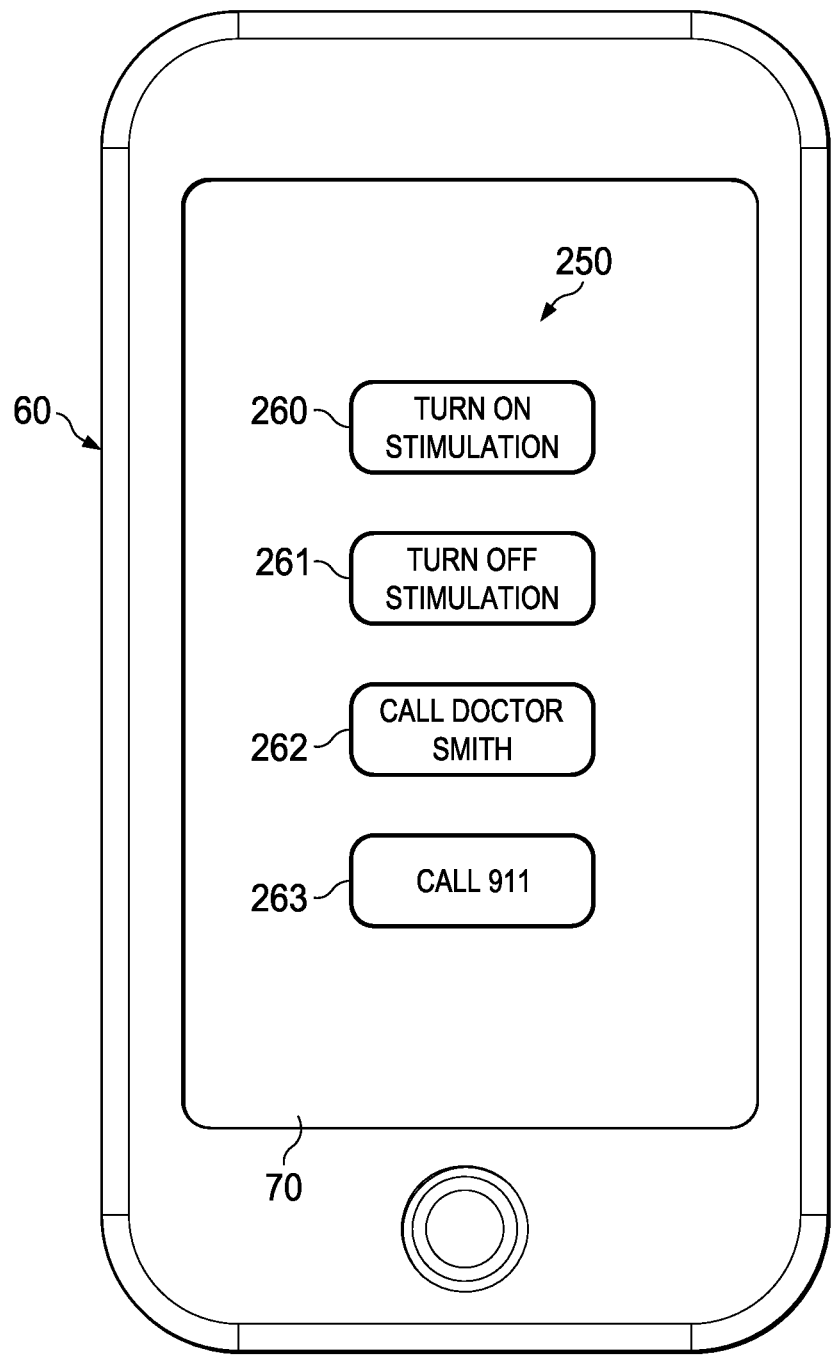

For example, referring now to FIG. 12, suppose a user is not the actual patient himself/herself, but is a person trusted by the patient, including but not limited to, a spouse of the patient, a parent of the patient, a child of the patient, a sibling of the patient, or even a friend of the patient. This trusted user may also have his/her biometric data registered with the mobile computing device 60 previously, and/or may also have his/her own passcode that is different from the actual patient's code or the medical professional's passcode. After this person has been authenticated as a trusted non-patient user, the mobile computing device 60 may display a user interface 250 that is different from the patient programmer user interface and the clinician programmer user interface discussed above, both in terms of visual design and the available level of access to the IMD 30.

In the embodiment shown in FIG. 12, the user interface 250 may display virtual buttons 260-263, which allow the user to turn on stimulation, turn off stimulation, call the doctor, and call 911, respectively. As such, the user interface 250 allows the trusted non-patient user to activate certain functions of the IMD (e.g., turning on/off stimulation) and to seek professional assistance (e.g., call the patient's doctor or 911) in cases of emergency, for example when the actual patient may be incapacitated or has difficulty operating the mobile computing device 60. However, the user interface 250 does not allow the trusted non-patient user to meddle or tinker with other functions of the IMD 30. Again, the user interface 250 illustrated in FIG. 12 is merely an example, and in other embodiments it may have different layouts and may offer different functionalities than those described above.

As another example, suppose the user is not the medical professional who is in charge of treating the patient, but is a first responder or other personnel who can provide pre-hospital care for the patient in cases of medical emergency. In some embodiments, the first responder may have a universal override code that can be used as an authentication or authorization code to unlock the mobile computing device 60 and to launch a user interface 270 after engaging the icon 180. In other embodiments, the first responder's biometric data (e.g., fingerprints) may also be used as an override code. Again, the user interface 270 that is automatically displayed to the first responder is different from the patient programmer user interface, the clinician programmer user interface, and the trusted non-patient user's interface discussed above, both with respect to its visual layout/design and the available level of access to the IMD 30.

Figure 13:
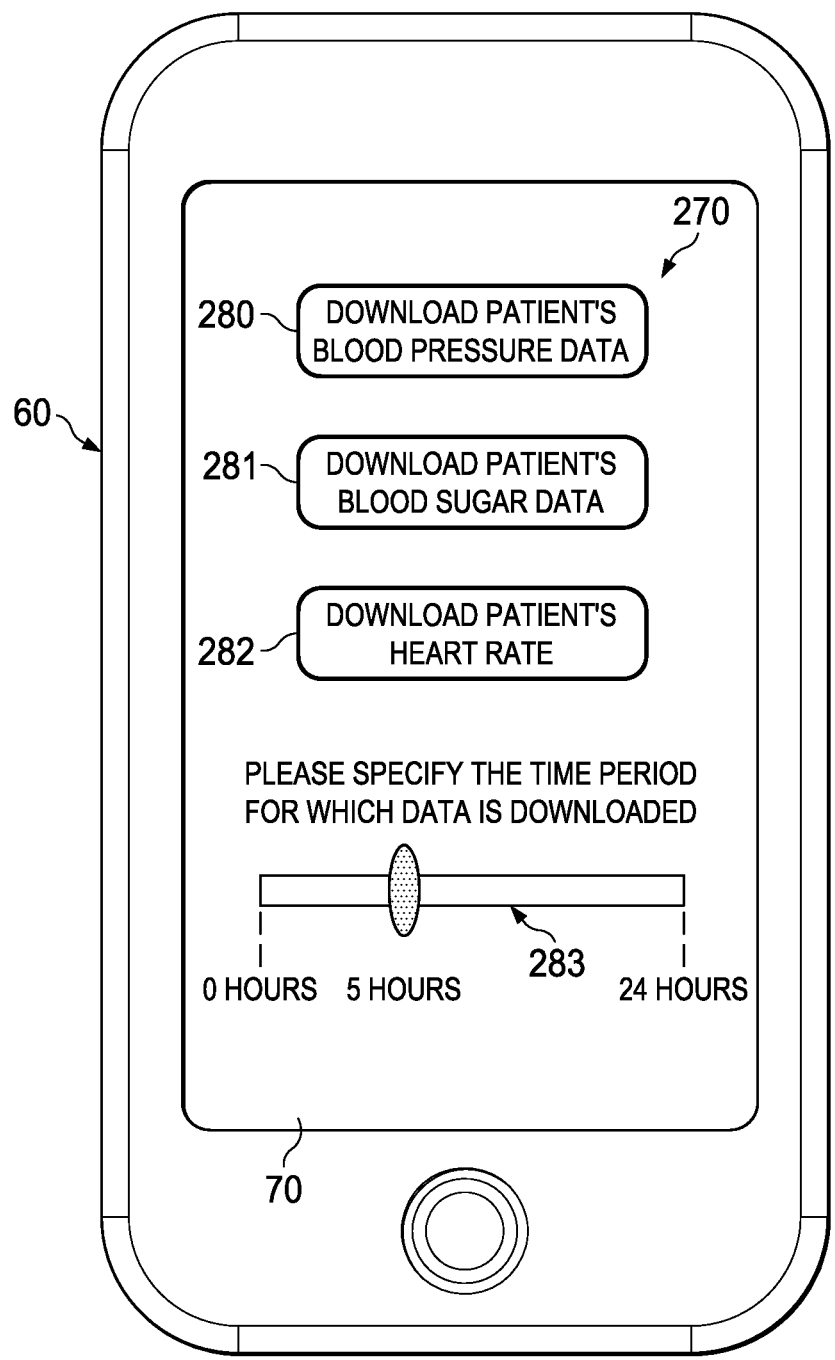

In the embodiment shown in FIG. 13, the user interface 270 displays virtual buttons 280-282 and a virtual control mechanism 283. The virtual buttons 280-282 allow the first responder user to download relevant physiological data from the patient, such as blood pressure, blood sugar, and heart rate. These types of patient physiological data may be collected by the IMD 30 itself, or may be collected by other sensors. The collected patient data may be periodically or continuously sent to the mobile computing device 60 for storage. In some embodiments, this data collection and storage process is "hidden" from the patient's perspective, as the patient need not necessarily be aware of it.

The virtual control mechanism 283 may include a slider that allow the first responder user to decide the time period in which the patient data should be downloaded, for example, the last 5 hours. The downloaded data may then be displayed in a separate screen (not illustrated herein), for example as a graph on the mobile computing device 60. This helps the first responder user make a diagnosis for the patient and possibly formulate an emergency treatment plan. The ability to download the patient's physiological data for a specified period of time may not be offered in the user interfaces for the patient and the trusted non-patient user, and may or may not be offered even in the clinician programmer user interface. Therefore, the present disclosure allows different users to automatically access different user interfaces with varying degrees of access to the IMD 30, which is not available in conventional systems.

It is also understood that the different privileges discussed above (e.g., privileges associated with controlling or operating the IMD 30 differently) may be assigned and/or reassigned via the web or a cloud-architecture. In other words, the privileges do not necessarily need to be defined by the portable electronic device 90, the IMD 30, or the mobile computing device 60. Instead, via these devices' network connections, the privileges for any given device (e.g., how the portable electronic device 90 may access the IMD 30) may vary day to day and may be adjusted when necessary.

It is also understood that the portable electronic device 90 may implement certain safety controls to enhance the security and operability of the system 20A. For example, in some embodiments, the portable electronic device 90 may be configured with predefined stimulation parameter thresholds. During operation, the portable electronic device 90 will inspect the data (e.g., containing the commands to operate the IMD 30) received from the mobile computing device 60 to see if any of the commands would cause one or more of the predefined stimulation parameter thresholds to be violated.

As an example, the portable electronic device 90 may be configured to store in the memory storage therein a list of stimulation parameter ranges. Anything above or below that range is deemed unsafe for the patient and should be rejected. For instance, a stimulation current may have a range from about 1 mA to about 15 mA. If the portable electronic device 90 receives data that indicates that the user has entered a stimulation current of 17 mA, then the portable electronic device 90 will not allow the data to be forwarded to the IMD 30 for programming thereof. Instead, the portable electronic device 90 may communicate with the mobile computing device 60 to cause it to display a warning or error message for its user. In this manner, the portable electronic device 90 ensures the overall safety of the patient and the feasibility of the system 20A.

Figure 14:
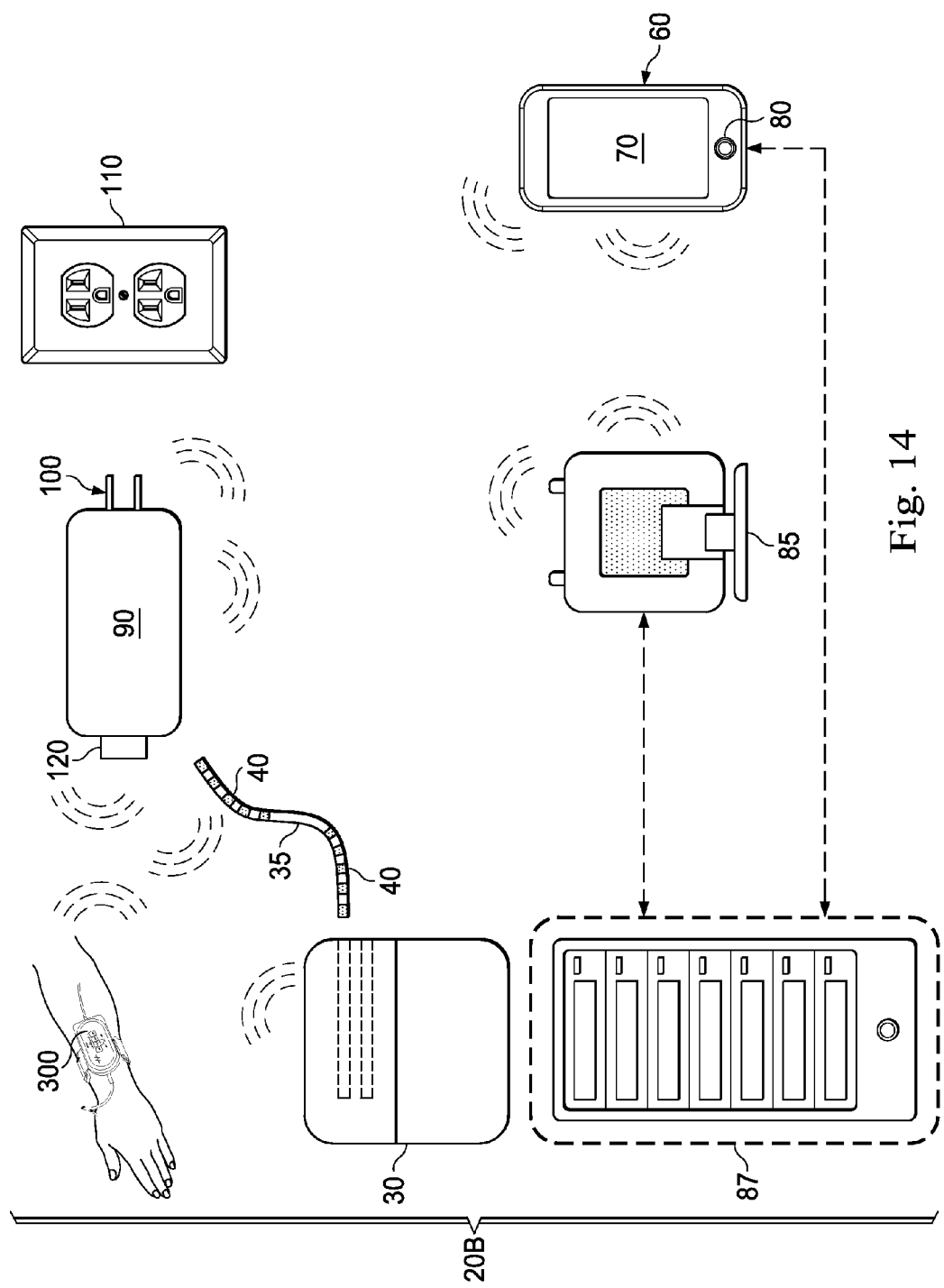

FIG. 14 illustrates a simplified diagrammatic view of a system 20B of the present disclosure according to an alternative embodiment. For reasons of consistency and clarity, similar components in the system 20A shown FIGS. 1-3 and the system 20B shown in FIG. 14 are labeled the same. For example, the system 20B includes the IMD 30 for providing a medical therapy to a target patient, the mobile computing device 60 for providing a plurality of distinct user interfaces (each with a different level of access to the IMD 30) for interacting with the IMD 30, and a portable electronic device 90 for establishing communications pathways between the IMD 30 and the mobile computing device 60.

The system 20B further includes a wearable medical device 300. The wearable medical device 300 may include one or more sensors configured to measure the physiological data of a patient (on whom the medical device 300 is worn). For example, the wearable medical device 300 may include sensors configured to measure the patient's heart rate, respiration rate, blood pressure, body temperature, skin moisture, blood sugar, blood glucose, electrophysiological signals such as EKG, electroencephalography (EEG), or electromyography (EMG), the patient's motions/movement/posture, muscle contractions, etc. After being gathered, the patient's physiological data may be analyzed locally on the wearable medical device 300, or it may be sent to the portable electronic device 90 or the mobile computing device 60 for further analysis.

The wearable medical device 300 may have a plurality of form factors, such as patches, adhesive patches, wrist bands, sleeves, vests, gloves, jackets, helmets, goggles, glasses, or any small portable boxes or sticks that can be securely attached to the patient. To facilitate the attachment of the wearable medical device 300 to the body of the patient, the wearable medical device may use straps, strings, adhesives, suction mechanisms, etc. The wearable medical device 300 may also include a padding material for patient comfort.

To facilitate the communication with external devices such as the portable electronic device 90, the mobile computing device 60, or the IMD 30, the wearable medical device 300 may include one or more transceivers (e.g., Wi-Fi transceiver, Bluetooth transceiver, MICS transceiver, etc.). In some embodiment, the wearable medical device 300 is configured for unidirectional communication with the IMD 30 such that the wearable medical device 300 is configured to receive signals from (but not transmit signals to) the IMD 30.

In another embodiment, the wearable medical device 300 is configured for bidirectional communication with the IMD 30 such that the wearable medical device 300 is configured to receive signals from the IMD 30 and transmit signals to the IMD 30. The unidirectional or bidirectional communication may be performed using well known medical device RF communication means and protocol such as MICS, Telemetry A, Telemetry B, or Telemetry C.

The wearable medical device 300 may further include components such as: one or more antennas/coils for sending and receiving wireless signals, a memory storage for storing programming instructions, a microcontroller or microprocessor for executing the programming instructions, a camera for taking pictures and/or videos, and rechargeable battery or another suitable power source.

According to some embodiments, the IMD 30 and the wearable medical device 300 are collectively configured to generate an alert signal. The alert signal may be indicative of a problem having been detected with the functionality of the IMD 30. The alert signal may also be indicative of a specific condition relating to the patient's health being detected (for example in response to an analysis of the physiological data being gathered by the wearable medical device 300). The alert signal may be sent to the mobile computing device 60 either directly via the transmitter of the wearable medical device 300, or via the portable electronic device 90.

Upon receipt of the alert signal, the mobile computing device 60 may generate an audible notification using its speakers, a vibratory notification (e.g., buzzing), or a visual notification on the screen 70, so as to inform the user of the mobile computing device 60 of the alert signal being generated and received. In other words, the audible/vibratory/visual notification generated by the mobile computing device 60 lets the user know that there is a potential problem with either the IMD 30 or the patient (which may be the user himself/herself), and that the potential problem should be further examined to determine whether or not it needs to be solved.

In some embodiments, the mobile computing device 60 may also forward the alert signal to the local server/router 85, which is configured to forward the signal to the remote server 87. The remote server may have a predetermined IP address. Alternatively, the mobile computing device 60 may directly forward the alert signal to the remote server 87. In some other embodiments, the portable electronic device 90 may bypass the mobile computing device 60 and may send the alert signal to the local server 85 directly, which will then forward the alert signal to the remote server 87.

In response to the receipt of the alert signal, the remote server 87 may be configured to alert a healthcare provider of the patient wearing the wearable medical device 300. The remote server 87 may also alert an emergency service personnel. The healthcare provider and/or the emergency service personnel may remotely adjust one or more parameters associated with the delivery of the medical therapy by the IMD 30. The healthcare provider and/or the emergency service personnel may also remotely program, re-program, or update software or firmware loaded in the IMD 30 and/or the wearable medical device 300.

In some embodiments, the IMD 30 can be configured to issue only a limited number of alerts under certain circumstances. The IMD 30 can also be configured to switch into a special "dumbed-down" communication mode that is adapted especially for communication with the wearable medical device 300 or with the portable electronic device 90, and not for communicating with a conventional CP or a PP. For example, once communication has been established and confirmed between the IMD 30 and the wearable medical device 300, the IMD 30 can be configured to send a first sequence of pulses, a second sequence of pulses, and so on, where each sequence is associated with a predetermined condition or state of the patient or device. These sequences may be stored in the memory storage of the wearable medical device 300. The stored sequences of pulses may be compared with the received sequences of pulses to determine which alert should be issued by the wearable medical device 300 to the mobile computing device 60 or the local server 85.

Non-limiting examples of alerts and other information include reminders that a patient follow-up with a healthcare provider is required or overdue, IMD and/or lead status according to a predetermined schedule, detection of low IMD battery life, impending IMD failure, and/or detection of a patient medical condition that requires immediate care (e.g., a heart arrhythmia, stroke, dangerously low or high blood pressure, lead dislodgement, etc.), or information provided according to a predetermined schedule regarding device performance or patient health status.

In some embodiments, the wearable medical device 300 and the portable electronic device 90 may be integrated into a single device, or packaged into a single package so as to appear as one device. Appropriately configured, the wearable medical device 300 and the portable electronic device 90 can replace, supersede, or complement, certain functionalities currently provided by conventional CPs and/or PPs, and potentially can do so at much lower cost. For example as discussed above, by leveraging the processing power and display of the mobile computing device 60, costly components directed to providing a user interface and other related processing tasks in conventional programmers can now be omitted from the wearable medical device 300 and the portable electronic device 90. Furthermore, the small physical distance between the wearable medical device 300 and the IMD 30 minimizes communication power consumption requirements for the wearable medical device 300 and the IMD 30. In some embodiments, the circuitry inside the wearable medical device 300 may also be configured to operate in a sleep mode until a wake-up signal is issued by the IMD 30, thereby further reducing power consumption and prolonging battery life.

The system 20B also offers other advantages in addition to lower costs. Because the wearable medical device 300 can be worn over the IMD 30 continuously, alerts or other important information can be received from the IMD 30 and provided to the patient or healthcare provider at any time (e.g., in real time), as opposed to only when a conventional electronic programmer is positioned over the IMD 30. The wearable medical device 300 can also be employed to reduce the number of times a patient must visit a healthcare facility just so that the patient and/or the IMD 30 can be monitored or checked, thereby reducing healthcare-related costs, as well as patient travel time and expense.

Figure 15:
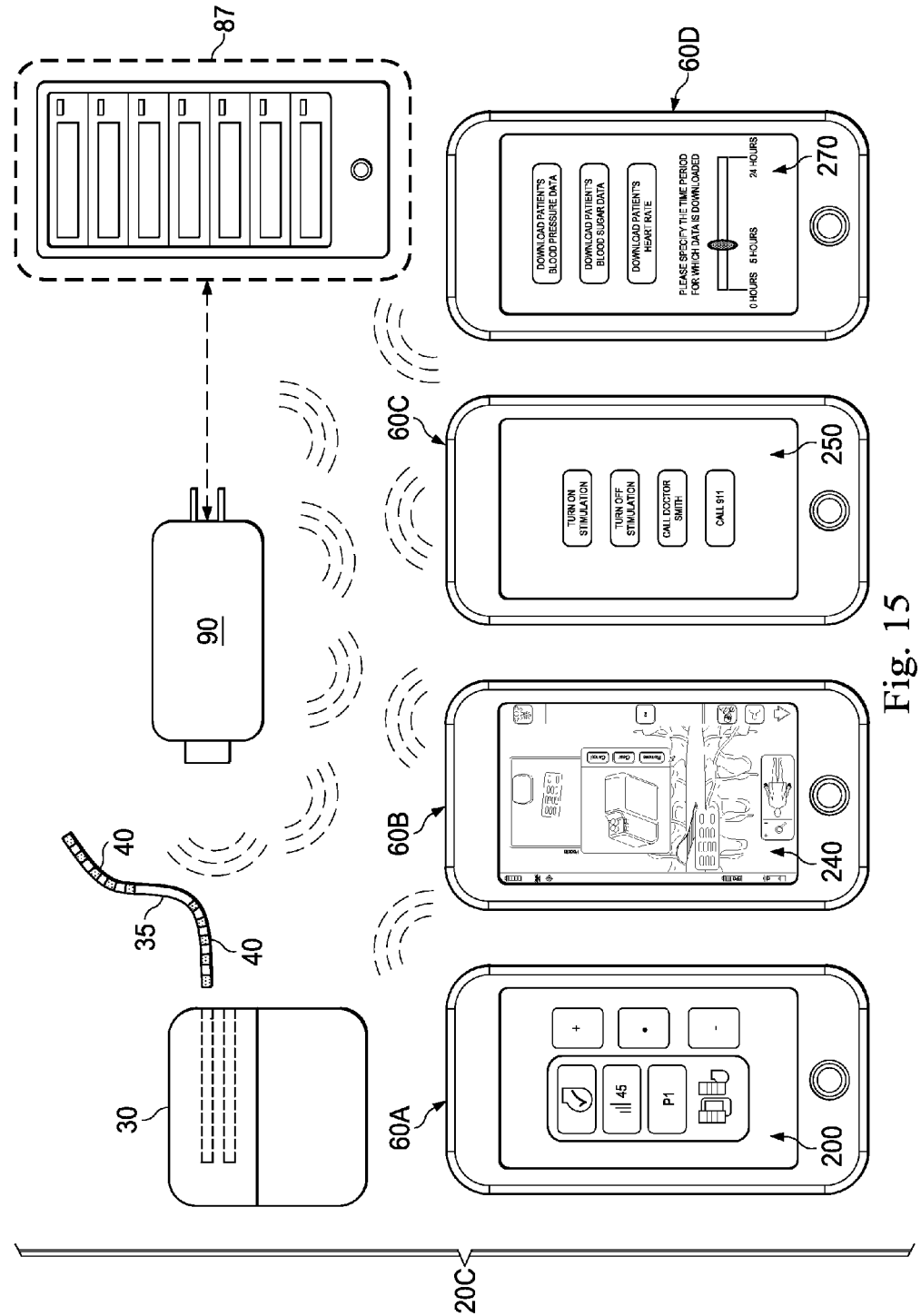

FIG. 15 illustrates a simplified diagrammatic view of another system 20C of the present disclosure according to an alternative embodiment. For reasons of consistency and clarity, similar components in the system 20A shown FIGS. 1-3 and the system 20C shown in FIG. 15 are labeled the same. For example, the system 20C includes the IMD 30 for providing a medical therapy to a target patient, a portable electronic device 90 for establishing communications pathways between the IMD 30 and external computing devices, and the remote server 87 communicatively coupled to the portable electronic device 90. The local server 85 (for example as a link between the portable electronic device 90 and the remote server 87) may be included in the system 20C but is not illustrated herein for reasons of simplicity.

However, instead of having just one mobile computing device 60, the system 20C includes a plurality of mobile computing devices, for example mobile computing devices 60A, 60B, 60C, and 60D. In the illustrated embodiment, each of the mobile computing devices 60A-60D belongs to a different user. For example, the mobile computing device 60A belongs to a patient user, the mobile computing device 60B belongs to a medical professional user, the mobile computing device 60C belongs to a trusted non-patient user, and the mobile computing device 60D belongs to a first responder user. Again, these are just examples. In other embodiments, one or more portable electronic devices 90 may function as de facto routers to establish a plurality of different communications pathways between a plurality of mobile computing devices 60 and a plurality of IMDs 30, as discussed above.

Each of these mobile computing devices 60A-60D has already gone through a registration process with the portable electronic device 90. The registration process may specify, among other things, the intended user of the mobile computing device 60A/B/C/D, and what level of access the mobile computing device should have with the IMD 30. In some embodiments, the registration process may include a pairing process, such as pairing over Bluetooth.

In other embodiments, the registration process may include displaying a plurality of questions on the mobile computing device, and providing answers to those questions. In various embodiments, the answers may include identification of the mobile computing device 60A/B/C/D, for example its Media Access Control (MAC) address, Mobile Equipment Identifier (MEID), Electronic Serial Number (ESN), International Mobile Station Equipment Identity (IMEI), or product number and serial number. In certain embodiments, the questions and answers may also include authentication information for each user, such as a passcode or biometric data belonging to the user. The answers to the questions (for example the user-supplied authentication information) may be saved locally on the memory storage of the portable electronic device 90 in some embodiments, or may be saved remotely in a remote server 87 communicatively coupled to the portable electronic device 90 in other embodiments.

Thereafter, after being authenticated, a user may launch the application (for example by pressing the icon 180 in FIG. 6) to control or configure the IMD 30 on his/her own mobile computing device 60A/B/C/D. The launching of the application may require the user to supply a passcode, a biometric scan, or some other form of authentication information. The user-supplied information may be compared with the authentication information saved locally on the portable electronic device 90 itself, or may be compared with the authentication saved remotely on the remote server 87 (via the portable electronic device 90). The user is then authenticated accordingly, or is denied access if the identity of the user has no match on file.

Depending on the authenticated identity of the user, the application will launch the "correct" user interface that is intended for the particular user. For example, the user accessing the mobile computing device 60A has been authenticated as the patient, and therefore the mobile computing device 60A automatically displays the patient programmer user interface 200 (shown and discussed in detail with reference to FIG. 8A) that is designed for the patient user. The user accessing the mobile computing device 60B has been authenticated as the medical professional, and therefore the mobile computing device 60B automatically displays the clinician programmer user interface 240 (shown and discussed in detail with reference to FIG. 10A) that is designed for the medical professional user. The user accessing the mobile computing device 60C has been authenticated as the person trusted by the patient (e.g., family or friend), and therefore the mobile computing device 60C automatically displays the clinician programmer user interface 250 (shown and discussed in detail with reference to FIG. 12) that is designed for the trusted non-patient user. The user accessing the mobile computing device 60D has been authenticated as the first responder, and therefore the mobile computing device 60D automatically displays the clinician programmer user interface 270 (shown and discussed in detail with reference to FIG. 13) that is designed for the first responder user.

As discussed above, the user interfaces 200, 240, 250, and 270 respectively displayed on the mobile computing devices 60A/B/C/D not only have different visual characteristics and layout design, but they also provide different levels of access to the IMD 30. In this manner, the portable electronic device 90 (or the remote server 87) serves as a "gate-keeper" of the system 20C in that it determines the appropriate level of access to the IMD 30 for each of the mobile computing devices 60A/B/C/D. This scheme allows for more flexibility. For example, if a user loses his/her mobile computing device, he/she merely needs to acquire a new mobile computing device (not necessarily the same type as the one he/she previously owned). The user can then register the new mobile computing device with the portable electronic device 90 and/or with the remote server 87. Thereafter, the user can then begin using the new mobile computing device as the programmer for interacting with the IMD 30.

Again, the replacement mobile computing device would be typically cheaper to purchase than a conventional clinician programmer or patient programmer, and the delay associated with the purchase of the replacement mobile computing device is minimal compared to the delay of obtaining a replacement clinician/patient programmer. Of course, it is understood that the system 20C also allows the user to deregister the previous mobile computing device so that it can no longer access the IMD 30 at all.

As another example, a healthcare facility having a plurality of healthcare professionals may have one or more mobile computing devices (e.g., iPads®) at the facility. These mobile computing devices may belong to the healthcare facility as a while and not necessarily with different users. Each of the healthcare professionals at this healthcare facility may be able to use any one of these mobile computing devices, and each of these mobile computing devices have already been registered with the portable electronic device 90.

Suppose that the patient (carrying the portable electronic device 90) goes to visit the healthcare facility. For whatever reason, the primary healthcare professional who usually attends to the patient is unavailable that day. Here, another healthcare professional may locate and use any one of the mobile computing devices of the healthcare facility to launch the clinician programmer user interface 240 to program or configure the IMD 30 inside the patient. In some embodiments, the mobile computing device used by the healthcare professional may also download relevant patient data or programming data from the mobile computing device of the patient, or from the portable electronic device 90 (in embodiments where the patient data or programming data are stored therein). It can be seen in the above example that the system 20C offers both the healthcare professionals and the patient more flexibility in terms of providing patient medical services.

The various embodiments discussed above with reference to FIGS. 1-15 pertain to providing different levels of access to the IMD 30 and their associated user interfaces on a mobile computing device 60. In these embodiments, the mobile computing device 60 (and/or the portable electronic device 90) may command the IMD 30 to perform different tasks. However, it is understood that in some alternative embodiments, the mobile computing device 60 and/or the portable electronic device 90 are configured as merely viewing devices. In other words, they may query information from the IMD 30, but are not allowed to command the IMD 30.

Figure 16:
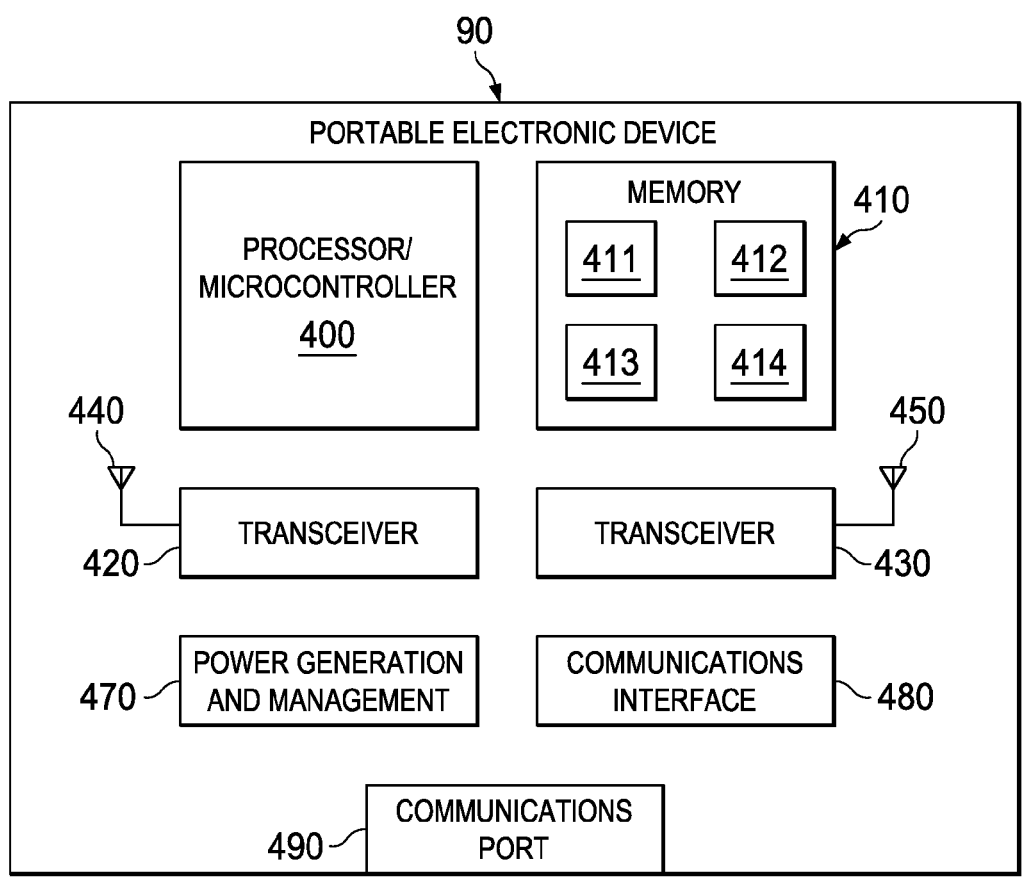
FIG. 16 is a simplified block diagram of a portable electronic device that is a part of the medical systems of FIGS. 1-3 and 14-15 according to various embodiments of the present disclosure.

FIG. 16 illustrates a simplified block diagram of the portable electronic device 90 discussed above according to one example embodiment. The portable electronic device 90 includes a printed circuit board ("PCB") that is populated with a plurality of electrical and electronic components that provide power, operational control, and protection to the portable electronic device 90. One of the electronic components implemented on the PCB is a processor/microcontroller 400. The processor/microcontroller 400 controls various operations of the portable electronic device 90. For example, the processor/microcontroller 400 may repackage or reformat the data received from the mobile computing device 60 into a format and/or frequency that can be sent to the IMD 30, or vice versa. As another example, the processor/microcontroller 400 may also perform the authentication of the user of the mobile computing device 60, or assist the mobile computing device 60 in the authenticating of the user.

In one example embodiment, the processor/microcontroller 400 is an applications processor model i.MX515 available from Free scale Semiconductor®. More specifically, the i.MX515 applications processor has internal instruction and data caches, multimedia capabilities, external memory interfacing, and interfacing flexibility. Further information regarding the i.MX515 applications processor can be found in, for example, the "IMX510EC, Rev. 4" data sheet dated August 2010 and published by Free scale Semiconductor® at www.freescale.com. The content of the data sheet is incorporated herein by reference. Of course, other processing units, such as other microprocessors, microcontrollers, digital signal processors, etc., can be used in place of the processor/microcontroller 400.

The portable electronic device 90 includes memory 410. In the illustrated embodiment, the memory 410 is implemented external to the processor/microcontroller 400. In other embodiments, the memory 410 may be implemented to the processor/microcontroller 400, or partially within the processor/microcontroller 400. The memory 410 may include a read-only memory ("ROM"), a random access memory ("RAM"), an electrically erasable programmable read-only memory ("EEPROM"), a FLASH memory, a hard disk, an optical disk, or another suitable magnetic, optical, physical, or electronic memory device. In some embodiments, the memory 410 includes a double data rate (DDR2) synchronous dynamic random access memory (SDRAM) for storing data relating to and captured during the operation of the portable electronic device 90. In some embodiments, the memory 410 may include a memory card slot for receiving an external memory card, for example a card slot that is configured to receive a secure digital (SD) multimedia card (MMC) or a MicroSD card. These card slots may be used to transfer data between the portable electronic device 90 and external devices. Of course, other types of data storage devices may be used in place of the data storage devices discussed herein.

The memory 410 is configured to store programming instructions (or software code) therein, which can be executed by the processor/microcontroller 400 to perform certain tasks. For example, in some embodiments, the software application for launching the various different user interfaces on the mobile computing device 60 to control the IMD 30 may be stored in the memory 410, or at least partially stored in the memory 410. The processor/microcontroller 400 executes this software application to initiate the launching of the user interface on the mobile computing device (which may include an authentication step in some embodiments).

Other examples of software that may be stored in the memory 410 of the portable electronic device 90 may include, but are not limited to, firmware, one or more applications, program data, one or more program modules, and other executable instructions. Again, the processor/microcontroller 400 is configured to retrieve from memory 410 and execute, among other things, instructions related to the control processes and methods described in the present disclosure.

In some embodiments, such as in the embodiment illustrated in FIG. 16, the memory 410 may also include a plurality of different memory partitions, for example memory partitions 411-414. The memory partitions 411-414 may each contain different information, such as information associated with accessing different parts of the IMD 30. The memory partitions 411-414 may be unlocked in response to different users being authenticated. For example, if the user accessing the mobile computing device 60 is a patient, the authentication of such user may unlock access to the memory partition 411, but not the rest of the memory partitions 411-414. The unlocked memory partition 411 may contain programming instructions that allows the patient user to have basic levels of access to the IMD 30. The basic levels of access to the IMD 30 may be represented by the patient programmer interface 200 discussed above. On the other hand, if the user accessing the mobile computing device 60 is a healthcare professional, the authentication of such user may unlock access to the memory partition 412. The unlocked memory partition 412 may contain programming instructions that allows the healthcare professional user to have advanced levels of access to the IMD 30. The advanced levels of access to the IMD 30 may be represented by the clinician programmer interface 240 discussed above. In addition, the authentication of the healthcare professional user may or may not unlock the access to the memory partition 411. Along the same lines, the authentication of other types of users (such as a trusted family/friend user or a first responder user) may also unlock the memory partitions 413 and 414, respectively, which in turn gives the user different levels of access to the IMD 30.

The portable electronic device 90 includes a transceiver 420 and a transceiver 430. The transceivers 420 and 430 may each include a plurality of microelectronic components such as switches, filters, low-noise amplifiers, digital-to-analog (DAC) converters, analog-to-digital (ADC) converters, mixers, amplifiers, oscillators, phase-locked loops (PLLs), etc. One or more of these electronic circuitry components may be integrated into a single discrete device or an integrated circuit (IC) chip.

The transceiver 420 is configured to conduct telecommunications with the IMD 30 under a first communications protocol, for example the MICS protocol. The transceiver 430 is configured to conduct telecommunications with the mobile computing device 60 or with the local server/router 85 under a second communications protocol, for example the Wi-Fi protocol, the Bluetooth protocol, or various cellular protocols. The first and second communications protocols employ different modulation/demodulation techniques and utilize different frequency bands. In some embodiments, the transceiver 420 may include (or may be coupled to) an antenna 440 that is optimized for sending and receiving signals to and from the IMD 30 under a first frequency used by the first communications protocol, and the transceiver 430 may include (or may be coupled to) an antenna 450 that is optimized for sending and receiving signals to and from the mobile computing device 60 under a second frequency used by the second communications protocol. Also, although not specifically illustrated for reasons of simplicity, the antennas 440 and 450 may each include a plurality of coils or windings.

Using the transceivers 420 and 430, the portable electronic device 90 is able to repackage the data received from the mobile computing device 60 into a format understood by the IMD 30 and transmit the repackaged data to the IMD 30, and vice versa. As such, the portable electronic device 90 may serve as a communications link or pathway between the IMD 30 and the mobile computing device 60. The transceivers 420 and 430 also allow the portable electronic device 90 to communicate with the local server/router 85 (FIGS. 1-3 and 14), and thus with the remote server 87 (FIGS. 1-3 and 14-15). Therefore, in case the mobile computing device 60 is unavailable, the portable electronic device 90 may directly communicate with the remote server 87 to upload or download data to and from the remote server.

The portable electronic device 90 further includes a power generation and management block 470. The power generation and management block 470 may include a power source (e.g., a lithium-ion battery) and a power supply for providing multiple power voltages to the processor/microcontroller 400, the memory 410, the transceivers 420/430, and peripherals. The battery may be rechargeable through either a connection to a wall outlet or by an induction charging mechanism. In some embodiments, the power generation and management block 470 is configured to provide charge for the mobile computing device 60. In other words, the power generation and management block 470 allows the portable electronic device 90 to serve as an extended battery for the mobile computing device 60.

In some embodiments, the portable electronic device 90 may also include a communications interface 480. In some embodiments, the communications interface may include more sophisticated components such as a biometric data scanner configured to obtain the biometric data from a user (such as the user's fingerprints, etc.), or a dedicated or virtual keyboard that allows the user to supply a passcode. In some other embodiments, the biometric data scanner and/or the keyboard may be omitted to save costs. The communications interface 480 may also include a liquid crystal display (LCD) panel or may include one or more light-emitting diodes (LEDs) to communicate basic statuses of the portable electronic device 90 (or of the system 30), such as its power/battery level, whether it is communicating with the IMD 30, or whether it is communicating with the mobile computing device 60, etc. In some embodiments, the communications interface may also include one or more audible components such as speakers or microphones configured to interact with the user audibly.

The portable electronic device 90 may include one or more communications ports 490 for wired communication. For example, one of the communications ports 490 may be the port 120 discussed above with reference to FIGS. 1-2. Again, the communications ports 490 may allow the portable electronic device 90 to conduct communications with the mobile computing device 60 (or other external devices) via a physical connection, and as such may at least in part replace the functionalities of the transceiver 430 (when such physical connection is actually made). In various embodiments, these communications ports 490 ports may include, but are not limited to, universal serial bus (USB) ports, microUSB ports, High Definition Multimedia Interface (HDMI) ports, FireWire ports, Joint Test Action Group (JTAG) ports, universal asynchronous receiver/transmitter (UART) ports, etc.

Figure 17:
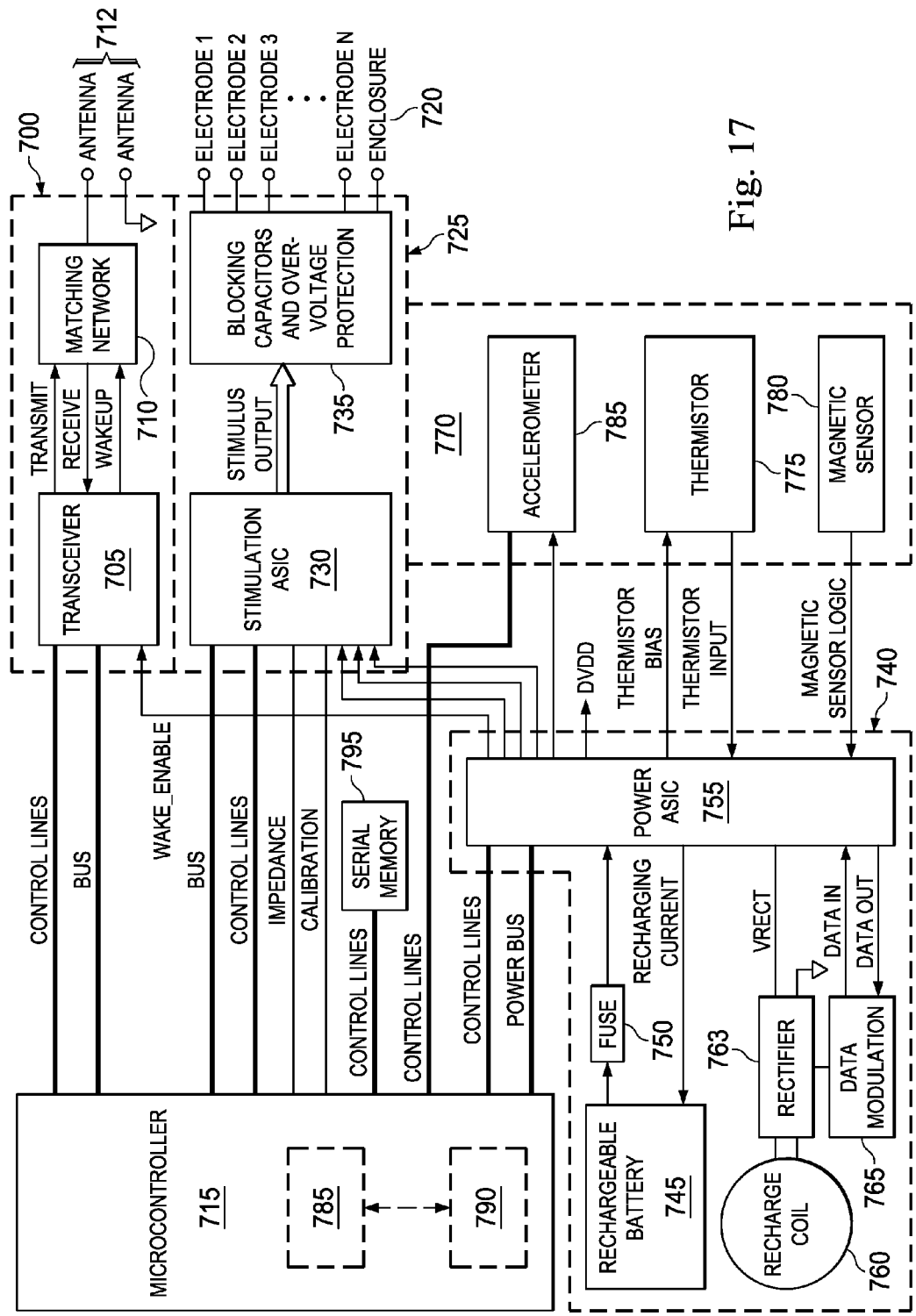
FIG. 17 is a simplified block diagram of an example implantable medical device that is a part of the medical systems of FIGS. 1-3 and 14-15 according to various embodiments of the present disclosure.

Although not specifically illustrated, the portable electronic device 90 also includes input/output ("I/O") systems that include routines for transferring information between components within the processor/microcontroller 400 and other components of the portable electronic device 90 or external to the portable electronic device 90. Other circuitry components may be used to c FIG. 17 shows a simplified block diagram of one example embodiment of the IMD 30 according to various aspects of the present disclosure. In the embodiment shown in FIG. 17, the IMD 30 includes an implantable pulse generator (IPG). The IPG includes a printed circuit board ("PCB") that is populated with a plurality of electrical and electronic components that provide power, operational control, and protection to the IPG. With reference to FIG. 17, the IPG includes a communication portion 700 having a transceiver 705, a matching network 710, and antenna 712. The communication portion 700 receives power from a power ASIC (discussed below), and communicates information to/from the microcontroller 715 and a device (e.g., the portable electronic device 90) external to the IPG. For example, the IPG can provide bi-direction radio communication capabilities, including Medical Implant Communication Service (MICS) bi-direction radio communication following the MICS specification.

The IPG provides stimuli to electrodes of an implanted medical electrical lead (not illustrated herein). As shown in FIG. 17, N electrodes are connected to the IPG. In addition, the enclosure or housing 720 of the IPG can act as an electrode. The stimuli are provided by a stimulation portion 225 in response to commands from the microcontroller 215. The stimulation portion 725 includes a stimulation application specific integrated circuit (ASIC) 730 and circuitry including blocking capacitors and an over-voltage protection circuit. As is well known, an ASIC is an integrated circuit customized for a particular use, rather than for general purpose use. ASICs often include processors, memory blocks including ROM, RAM, EEPROM, FLASH, etc. The stimulation ASIC 730 can include a processor, memory, and firmware for storing preset pulses and protocols that can be selected via the microcontroller 715. The providing of the pulses to the electrodes is controlled through the use of a waveform generator and amplitude multiplier of the stimulation ASIC 730, and the blocking capacitors and overvoltage protection circuitry 735 of the stimulation portion 725, as is known in the art. The stimulation portion 725 of the IPG receives power from the power ASIC (discussed below). The stimulation ASIC 730 also provides signals to the microcontroller 715. More specifically, the stimulation ASIC 730 can provide impedance values for the channels associated with the electrodes, and also communicate calibration information with the microcontroller 715 during calibration of the IPG.

The IPG also includes a power supply portion 740. The power supply portion includes a rechargeable battery 745, fuse 750, power ASIC 755, recharge coil 760, rectifier 763 and data modulation circuit 765. The rechargeable battery 745 provides a power source for the power supply portion 740. The recharge coil 760 receives a wireless signal from the PPC. The wireless signal includes an energy that is converted and conditioned to a power signal by the rectifier 763. The power signal is provided to the rechargeable battery 745 via the power ASIC 755. The power ASIC 755 manages the power for the IPG. The power ASIC 755 provides one or more voltages to the other electrical and electronic circuits of the IPG. The data modulation circuit 765 controls the charging process.

The IPG also includes a magnetic sensor 780. The magnetic sensor 780 provides a "hard" switch upon sensing a magnet for a defined period. The signal from the magnetic sensor 780 can provide an override for the IPG if a fault is occurring with the IPG and is not responding to other controllers.

The IPG is shown in FIG. 17 as having a microcontroller 715. Generally speaking, the microcontroller 715 is a controller for controlling the IPG. The microcontroller 715 includes a suitable programmable portion 785 (e.g., a microprocessor or a digital signal processor), a memory 790, and a bus or other communication lines. An exemplary microcontroller capable of being used with the IPG is a model MSP430 ultra-low power, mixed signal processor by Texas Instruments. More specifically, the MSP430 mixed signal processor has internal RAM and flash memories, an internal clock, and peripheral interface capabilities. Further information regarding the MSP 430 mixed signal processor can be found in, for example, the "MSP430G2x32, MSP430G2x02 MIXED SIGNAL MICROCONTROLLER" data sheet; dated December 2010, published by Texas Instruments at www.ti.com; the content of the data sheet being incorporated herein by reference.

The IPG includes memory, which can be internal to the control device (such as memory 790), external to the control device (such as serial memory 795), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The programmable portion 785 executes software that is capable of being stored in the RAM (e.g., during execution), the ROM (e.g., on a generally permanent basis), or another non-transitory computer readable medium such as another memory or a disc.

Software included in the implementation of the IPG is stored in the memory 790. The software includes, for example, firmware, one or more applications, program data, one or more program modules, and other executable instructions. The programmable portion 785 is configured to retrieve from memory and execute, among other things, instructions related to the control processes and methods described below for the IPG. For example, the programmable portion 285 is configured to execute instructions retrieved from the memory 790 for sweeping the electrodes in response to a programming signal.

It is understood that although an IPG is used herein to illustrate an example other types of IMDs may be implemented in other embodiments without departing from the scope of the present disclosure.

Figure 18B:
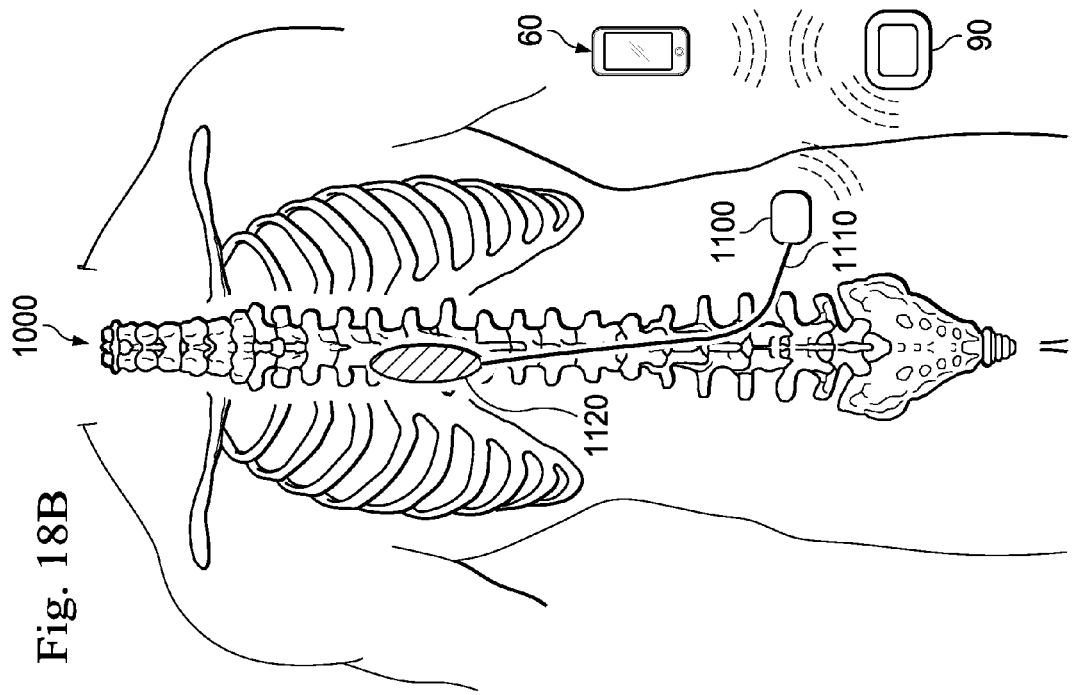
FIGS. 18A-18B illustrate an example medical context within which the various devices and systems of the present disclosure may be implemented.
Figure 18A:
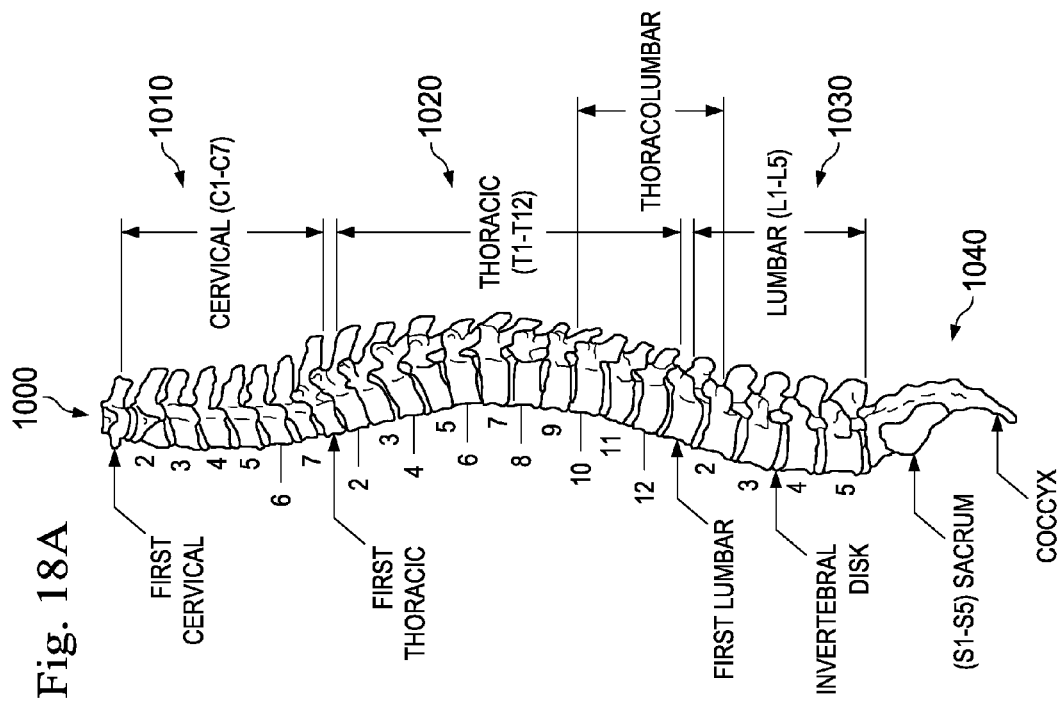

FIGS. 18A-18B illustrate an example medical context within which the various devices and systems of the present disclosure may be implemented. For example, FIG. 18A illustrates a side view of a human spine 1000, and FIG. 18B illustrate a posterior view of the spine 1000. The spine 1000 includes a cervical region 1010, a thoracic region 1020, a lumbar region 1030, and a sacrococcygeal region 1040. The cervical region 1010 includes the top 7 vertebrae, which may be designated with C1-C7. The thoracic region 1020 includes the next 12 vertebrae below the cervical region 1010, which may be designated with T1-T12. The lumbar region 1030 includes the final 5 "true" vertebrae, which may be designated with L1-L5. The sacrococcygeal region 1040 includes 9 fused vertebrae that make up the sacrum and the coccyx. The fused vertebrae of the sacrum may be designated with S1-S5.

Neural tissue (not illustrated for the sake of simplicity) branch off from the spinal cord through spaces between the vertebrae. The neural tissue can be individually and selectively stimulated in accordance with various aspects of the present disclosure. For example, referring to FIG. 18B, an IPG device 1100 (an example embodiment of the IMD 30) is implanted inside the body. The IPG device 1100 may include a neurostimulator device. A conductive lead 1110 is electrically coupled to the circuitry inside the IPG device 1100. The conductive lead 1110 may be removably coupled to the IPG device 1100 through a connector, for example. A distal end of the conductive lead 1110 is attached to one or more electrodes 1120. The electrodes 1120 are implanted adjacent to a desired nerve tissue in the thoracic region 1020. Using well-established and known techniques in the art, the distal end of the lead 1110 with its accompanying electrodes may be positioned along or near the epidural space of the spinal cord. It is understood that although only one conductive lead 1110 is shown herein for the sake of simplicity, more than one conductive lead 1110 and corresponding electrodes 1120 may be implanted and connected to the IPG device 1100.

The electrodes 1120 deliver current drawn from the current sources in the IPG device 1100, therefore generating an electric field near the neural tissue. The electric field stimulates the neural tissue to accomplish its intended functions. For example, the neural stimulation may alleviate pain in an embodiment. In other embodiments, a stimulator may be placed in different locations throughout the body and may be programmed to address a variety of problems, including for example but without limitation; prevention or reduction of epileptic seizures, weight control or regulation of heart beats.

It is understood that the IPG device 1100, the lead 1110, and the electrodes 1120 may be implanted completely inside the body, may be positioned completely outside the body or may have only one or more components implanted within the body while other components remain outside the body. When they are implanted inside the body, the implant location may be adjusted (e.g., anywhere along the spine 1000) to deliver the intended therapeutic effects of spinal cord electrical stimulation in a desired region of the spine.

According to the various aspects of the present disclosure, the IPG device 1100 may be controlled by the mobile computing device 60 via a communications link established at least in part via the portable electronic device 90, as discussed above. Again, in response to different users being authenticated, the mobile computing device 60 may display different user interfaces that have different levels of access to the IPG device 1100.

Figure 19:
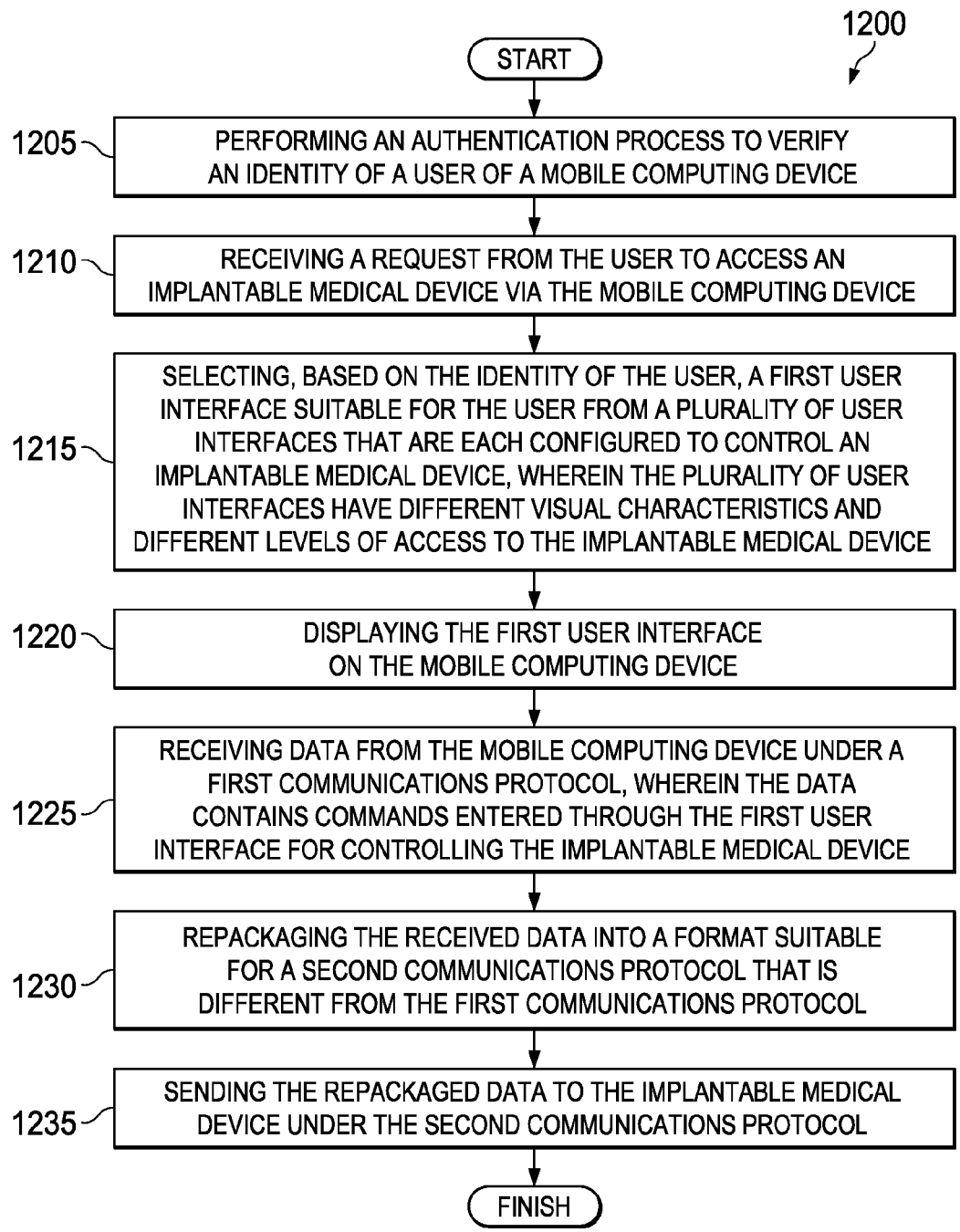
FIG. 19 is a simplified flowchart illustrating a method of storing a sensation map according to various aspects of the present disclosure.

FIG. 19 is a simplified flowchart of a method 1200 of communicating with an implantable medical device. The method 1200 includes a step 1205 of performing an authentication process to verify an identity of a user of a mobile computing device. In some embodiments, the authentication process comprises a password-based authentication or a biometric-scan-based authentication.

The method 1200 includes a step 1210 of receiving a request from the user to access an implantable medical device via the mobile computing device. It is understood that the order in which the steps 1205 and 1210 is performed is not important. In other words, in some embodiments, the step 1210 may be performed before the step 1205.

The method 1200 includes a step 1215 of selecting, based on the identity of the user, a first user interface suitable for the user from a plurality of user interfaces that are each configured to control an implantable medical device. The of user interfaces have different visual characteristics and different levels of access to the implantable medical device.

The method 1200 includes a step 1220 of displaying the first user interface on the mobile computing device.

The method 1200 includes a step 1225 of receiving data from the mobile computing device under a first communications protocol. The data contains commands entered through the first user interface for controlling the implantable medical device.

The method 1200 includes a step 1230 of repackaging the received data into a format suitable for a second communications protocol that is different from the first communications protocol.

The method 1200 includes a step 1235 of sending the repackaged data to the implantable medical device under the second communications protocol.

In some embodiments, one or more of the steps 1205-1235 are performed by a software application or program. The software application may be installed on the mobile computing device or on a portable electronic device communicatively coupled to the mobile computing device. In some embodiments, the software application may be offered (by its maker) for download and installation on a local device such as the mobile computing device. The offering may be done via an online apps store.

In some embodiments, one or more of the steps 1205-1235 are performed by a mobile computing device. In other embodiments, one or more of the steps 1205-1235 are performed by a portable electronic device communicatively coupled to the mobile computing device. In some embodiments, the portable electronic device includes: a first transceiver configured to perform the receiving of the data under the first communications protocol, a processor configured to perform the repackaging of the data, and a second transceiver configured to perform the sending of the data under the second communications protocol. In some embodiments, the portable electronic device has a form factor that is one of: a dongle and a case that each allow the portable electronic device to be directly attached to the mobile computing device. In some embodiments, the portable electronic device includes a battery. The battery may be used to charge the mobile computing device.

It is understood that additional process steps may be performed before, during, or after the steps 1205-1235. For example, the method 1200 may include the following steps: a step of performing a further authentication process to verify an identity of a further user of a mobile computing device, a step of receiving a request from the further user to access the implantable medical device via the mobile computing device, and a step of selecting, based on the identity of the further user, a second user interface suitable for the further user from the plurality of user interfaces. The second user interface is configured to offer the further user a more advanced level of access to the implantable medical device compared to the first user interface. The method 1200 may further include a step of displaying the second user interface on the mobile computing device. As another example, the method 1200 may further include a step of receiving physiological data from a wearable medical device worn by a patient, and a step of communicating an alert in response to the received physiological data.

Figure 20:
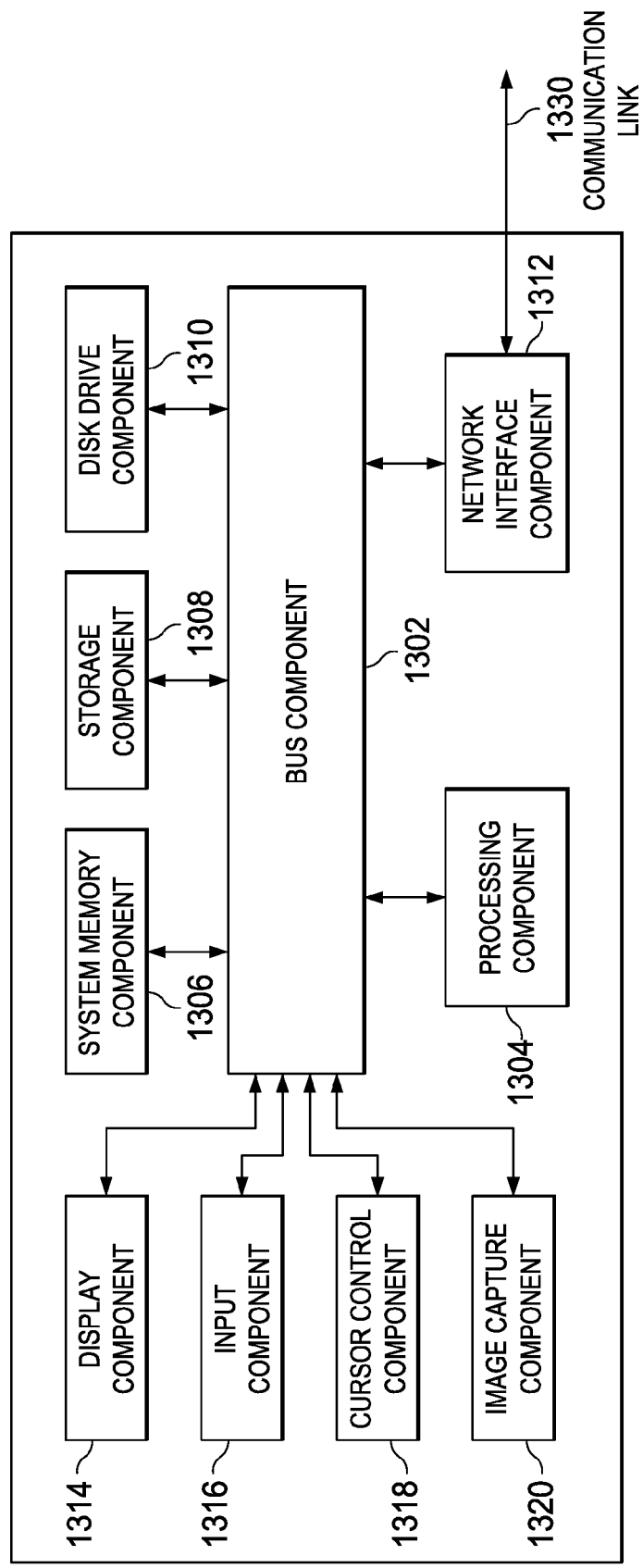
FIG. 20 is a simplified block diagram of a computer system for implementing various methods and devices described according to various aspects of the present disclosure.

FIG. 20 is a block diagram of a computer system 1300 suitable for implementing various methods and devices described herein, for example, the various method blocks of the method 1200 of FIG. 19. In various implementations, the mobile computing device 60, the portable electronic device 90, the IMD 30, the wearable medical device 300, the local server 85, or the remote server 87 discussed above may each be at least partially implemented as the computer system 1300 for communication with a network in a manner as follows.

In accordance with various embodiments of the present disclosure, the computer system 1300, such as a mobile communications device and/or a network server, includes a bus component 1302 or other communication mechanisms for communicating information, which interconnects subsystems and components, such as processing component 1304 (e.g., processor, micro-controller, digital signal processor (DSP), etc.), system memory component 1306 (e.g., RAM), static storage component 1308 (e.g., ROM), disk drive component 1310 (e.g., magnetic or optical), network interface component 1312 (e.g., modem or Ethernet card), display component 1314 (e.g., cathode ray tube (CRT) or liquid crystal display (LCD)), input component 1316 (e.g., keyboard), cursor control component 1318 (e.g., mouse or trackball), and image capture component 1320 (e.g., analog or digital camera). In one implementation, disk drive component 1310 may comprise a database having one or more disk drive components.

In accordance with embodiments of the present disclosure, computer system 1300 performs specific operations by processor 1304 executing one or more sequences of one or more instructions contained in system memory component 1306. Such instructions may be read into system memory component 1306 from another computer readable medium, such as static storage component 1308 or disk drive component 1310. In other embodiments, hard-wired circuitry may be used in place of (or in combination with) software instructions to implement the present disclosure.

Logic may be encoded in a computer readable medium, which may refer to any medium that participates in providing instructions to processor 1304 for execution. Such a medium may take many forms, including but not limited to, non-volatile media and volatile media. In one embodiment, the computer readable medium is non-transitory. In various implementations, non-volatile media includes optical or magnetic disks, such as disk drive component 1310 and volatile media includes dynamic memory, such as system memory component 1306. In one aspect, data and information related to execution instructions may be transmitted to computer system 1300 via a transmission media, such as in the form of acoustic or light waves, including those generated during radio wave and infrared data communications. In various implementations, transmission media may include coaxial cables, copper wire, and fiber optics, including wires that comprise bus 1302.

Some common forms of computer readable media includes, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, carrier wave, or any other medium from which a computer is adapted to read.

In various embodiments of the present disclosure, execution of instruction sequences to practice the present disclosure may be performed by computer system 1300. In various other embodiments of the present disclosure, a plurality of computer systems 1300 coupled by communication link 1330 (e.g., a communications network, such as a LAN, WLAN, PTSN, and/or various other wired or wireless networks, including telecommunications, mobile, and cellular phone networks) may perform instruction sequences to practice the present disclosure in coordination with one another.

Computer system 1300 may transmit and receive messages, data, information and instructions, including one or more programs (i.e., application code) through communication link 1330 and communication interface 1312. Received program code may be executed by processor 1304 as received and/or stored in disk drive component 1310 or some other non-volatile storage component for execution.

Where applicable, various embodiments provided by the present disclosure may be implemented using hardware, software, or combinations of hardware and software. Also, where applicable, the various hardware components and/or software components set forth herein may be combined into composite components comprising software, hardware, and/or both without departing from the spirit of the present disclosure. Where applicable, the various hardware components and/or software components set forth herein may be separated into sub-components comprising software, hardware, or both without departing from the scope of the present disclosure. In addition, where applicable, it is contemplated that software components may be implemented as hardware components and vice-versa.

Software, in accordance with the present disclosure, such as computer program code and/or data, may be stored on one or more computer readable mediums. It is also contemplated that software identified herein may be implemented using one or more general purpose or specific purpose computers and/or computer systems, networked and/or otherwise. Where applicable, the ordering of various steps described herein may be changed, combined into composite steps, and/or separated into sub-steps to provide features described herein.

The foregoing has outlined features of several embodiments so that those skilled in the art may better understand the detailed description that follows. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A medical system, comprising:
   an implantable medical device;
   a mobile computing device, the mobile computing device including a screen, wherein the mobile computing device is configured to display on the screen:
      in response to an authentication of a first user, a first user interface for controlling the implantable medical device based on one or more first commands received from the first user, the first user interface mimicking a user interface of a patient programmer device; and
      in response to an authentication of a second user, a second user interface for controlling the implantable medical device based on one or more second commands received from the second user, the second user interface mimicking a user interface of a clinician programmer device having a greater number of programming options than the patient programmer device and offers a greater level of access to the implantable medical device than the patient programmer device, wherein the first user interface and the second user interface have different visual appearances; and
   a portable electronic device, wherein the portable electronic device includes:
      a first communications component configured to conduct telecommunications with the implantable medical device under a first communications protocol; and
      a second communications component configured to conduct telecommunications with the mobile computing device under a second communications protocol different from the first communications protocol;
   and wherein the portable electronic device is configured to:
      perform a safety control inspection on the one or more first commands or second commands; and
      use the first and second communications components to relay the one or more first commands or the one or more second commands to the implantable medical device in response to the one or more first commands or second commands passing the safety control inspection.

2. The medical system of claim 1, wherein:
   the implantable medical device includes a neurostimulator configured to generate electrical pulses as a part of an electrical stimulation therapy;
   the first user interface, by mimicking the user interface of the patient programmer, is configured to adjust an amplitude of the electrical pulses and to turn on and off the electrical stimulation therapy; and
   the second user interface, by mimicking the user interface of the clinician programmer, is configured to create a pain map or a stimulation map on a human body model.

3. The medical system of claim 1, wherein the portable electronic device has a form factor that is configured for direct attachment with the mobile computing device.

4. The medical system of claim 3, wherein the form factor of the portable electronic device is one of: a dongle and a case.

5. The medical system of claim 3, wherein the portable electronic device further includes a battery configured to provide an electrical charge to the mobile computing device.

6. The medical system of claim 1, wherein the mobile computing device further comprises:
   a memory storage configured to store computer instructions; and
   one or more electronic processors configured to execute the computer instructions to cause the mobile computing device to perform a plurality of different tasks, one of the tasks being the authentication of the first user or the second user;
   and wherein the authentication includes one of: a password-based authentication and a biometric-scan-based authentication.

7. The medical system of claim 6, wherein the mobile computing device includes a mechanism configured to perform a biometric scan of the first user or the second user.

8. The medical system of claim 6, wherein the computer instructions stored on the memory storage includes a software application that, when executed by the one or more electronic processors, causes the screen to display one of: the first user interface and the second user interface.

9. The medical system of claim 1, further comprising: a wearable medical device configured to be worn by a patient; wherein:
   the wearable medical device includes one or more sensors each configured to collect physiological data from the patient;
   the wearable medical device includes a communications device configured to conduct telecommunications with at least one of: the portable electronic device and the mobile computing device; and
   the wearable medical device is configured to send, at least in part via the communications device, the physiological data collected from the patient to one of: the portable electronic device and the mobile computing device.

10. The medical system of claim 9, wherein the mobile computing device is configured to generate an alert in response to the physiological data received from the wearable medical device.

11. The medical system of claim 1, wherein the implantable medical device includes one of: a pacemaker, an implantable cardioverter-defibrillator, an implantable cardiac signal monitor, an implantable loop recorder, an implantable spinal cord stimulator, an implantable pelvic nerve stimulator, an implantable peripheral nerve stimulator, an implantable brain stimulator, and a gastric system stimulator.

12. The medical system of claim 1, wherein the mobile computing device includes a smart phone or a tablet computer.

13. A portable electronic apparatus for facilitating communication between an implantable medical device and a mobile computing device, the portable electronic apparatus comprising:
- a first communications component configured to conduct telecommunications with the implantable medical device under a first communications protocol;
- a second communications component configured to conduct telecommunications with the mobile computing device under a second communications protocol different from the first communications protocol;
- a memory component configured to store programming instructions; and
- a processor component configured to execute the programming instructions to perform the following steps:
  - selecting, based on an authentication of a first user, a first user interface for controlling the implantable medical device, wherein the first user interface mimics a user interface of a patient programmer device;
  - selecting, based on an authentication of a second user, a second user interface for controlling the implantable medical device, wherein the second user interface mimics a user interface of a clinician programmer device having a greater number of programming options than the patient programmer device and provides a greater level of access to the implantable medical device than the patient programmer;
  - receiving a request to transmit data from the mobile computing device to the implantable medical device;
  - performing a safety inspection on the data that is requested to be transmitted; and
  - denying the request to transmit the data in response to a failure of the safety inspection.

14. The portable electronic apparatus of claim 13, wherein the steps further comprise: instructing the mobile computing device to display the first user interface or the second user interface on a screen of the mobile computing device.

15. The portable electronic apparatus of claim 13, wherein the steps further comprises transmitting, to the mobile computing device, at least in part via the second communications component, information for displaying the first user interface or the second user interface on a screen of the mobile computing device.

16. The portable electronic apparatus of claim 13, wherein:
- the implantable medical device includes a neurostimulator configured to generate electrical pulses as a part of an electrical stimulation therapy;
- the first user interface, by mimicking the user interface of the patient programmer, is configured to adjust an amplitude of the electrical pulses and to turn on and off the electrical stimulation therapy; and
- the second user interface, by mimicking the user interface of the clinician programmer, is configured to create a pain map or a stimulation map on a human body model.

17. The portable electronic apparatus of claim 13, wherein the steps further comprise:
- receiving, via the first communications component, data from the mobile computing device under the first communications protocol, wherein the data contains commands entered through the first or second user interface for controlling the implantable medical device;
- repackaging, via the processor component, the received data into a format suitable for communication under the second communications protocol; and
- sending, via the second communications component, the repackaged data to the implantable medical device under the second communications protocol.

18. The portable electronic apparatus of claim 13, wherein the portable electronic apparatus has a form factor that is configured for direct attachment with the mobile computing device.

19. The portable electronic apparatus of claim 18, wherein the form factor of the portable electronic apparatus is one of: a dongle and a case.

20. The portable electronic apparatus of claim 18, wherein the portable electronic apparatus further includes a battery configured to provide an electrical charge to the mobile computing device.

21. The portable electronic apparatus of claim 13, wherein the portable electronic apparatus is configured to be electrically coupled to, and receive power from, a household power outlet.

22. The portable electronic apparatus of claim 13, wherein the portable electronic apparatus further comprises a communications interface configured to acquire a passcode or biometric data from a user.

23. The portable electronic apparatus of claim 13, wherein the portable electronic apparatus is further configured to: forward to the mobile computing device, via the first and second communications components, physiological data of a patient gathered by a wearable medical device.

24. A method of communicating with an implantable medical device, comprising:
- performing an authentication process to verify an identity of a user of a mobile computing device;
- receiving a request from the user to access an implantable medical device via the mobile computing device, wherein the receiving the request comprises receiving data from the mobile computing device under a first communications protocol, wherein the data contains commands entered through the first user interface for controlling the implantable medical device;
- repackaging the received data into a format suitable for a second communications protocol that is different from the first communications protocol;
- sending the repackaged data to the implantable medical device under the second communications protocol;
- selecting, based on the identity of the user, a first user interface suitable for the user from a plurality of user interfaces that are each configured to control an implantable medical device, wherein the plurality of user interfaces includes at least a user interface mimicking a user interface of a patient programmer device and a user interface mimicking a user interface of a clinician programmer device, wherein the clinician programmer device has a greater number of programming options than the patient programmer device and provides a greater level of access to the implantable medical device than the patient programmer device;
- displaying the first user interface on the mobile computing device;
- receiving a request from the mobile computing device to transmit data to the implantable medical device;
- performing a safety inspection on the data; and
- preventing a transmission of the data in response to a failure of the safety inspection.

25. The method of claim 24, wherein the performing, the receiving, the selecting, and the displaying are performed by a software application installed on the mobile computing device, wherein the method further comprises: offering the software application for download and installation on the mobile computing device.

26. The method of claim 24, wherein at least the receiving of the data, the repackaging of the data, and the sending of the repackaged data are performed by a portable electronic device communicatively coupled to the mobile computing device.

27. The method of claim 26, wherein the portable electronic device includes:
a first transceiver configured to perform the receiving of the data under the first communications protocol;
a processor configured to perform the repackaging of the data; and
a second transceiver configured to perform the sending of the data under the second communications protocol.

28. The method of claim 26, wherein the portable electronic device has a form factor that is one of: a dongle and a case that each allow the portable electronic device to be directly attached to the mobile computing device.

29. The method of claim 26, wherein the portable electronic device includes a battery, and wherein the method further comprises: charging the mobile computing device via the battery of the portable electronic device.

30. The method of claim 24, further comprising:
performing a further authentication process to verify an identity of a further user of a mobile computing device;
receiving a request from the further user to access the implantable medical device via the mobile computing device;
selecting, based on the identity of the further user, a second user interface suitable for the further user from the plurality of user interfaces, wherein the second user interface is configured to offer the further user a more advanced level of access to the implantable medical device compared to the first user interface; and
displaying the second user interface on the mobile computing device.

31. The method of claim 24, wherein the authentication process comprises a password-based authentication or a biometric-scan-based authentication.

32. The method of claim 24, further comprising:
receiving physiological data from a wearable medical device worn by a patient; and
communicating an alert in response to the received physiological data.

33. A non-transitory computer readable medium comprising executable instructions that when executed by a processor, causes the processor to perform the steps of:
performing an authentication process to verify an identity of a user of a mobile computing device;
receiving a request from the user to access an implantable medical device via the mobile computing device, wherein the receiving the request comprises receiving data from the mobile computing device under a first communications protocol, wherein the data contains commands entered through the first user interface for controlling the implantable medical device;
repackaging the received data into a format suitable for a second communications protocol that is different from the first communications protocol;
sending the repackaged data to the implantable medical device under the second communications protocol;
selecting, based on the identity of the user, a first user interface suitable for the user from a plurality of user interfaces that are each configured to control an implantable medical device, wherein the plurality of user interfaces includes at least a user interface mimicking a user interface of a patient programmer device and a user interface mimicking a user interface of a clinician programmer device, wherein the clinician programmer device has a greater number of programming options than the patient programmer device and provides a greater level of access to the implantable medical device than the patient programmer device;
displaying the first user interface on the mobile computing device;
receiving a request from the mobile computing device to transmit data to the implantable medical device;
performing a safety inspection on an electronic communication received from the mobile computing device on response to a request from the mobile computing device to transmit the electronic communication to the implantable medical device; and
preventing a transmission of the electronic communication in response to a failure of the safety inspection.

34. The non-transitory computer readable medium of claim 33, wherein the steps further comprise:
performing a further authentication process to verify an identity of a further user of a mobile computing device;
receiving a request from the further user to access the implantable medical device via the mobile computing device;
selecting, based on the identity of the further user, a second user interface suitable for the further user from the plurality of user interfaces, wherein the second user interface is configured to offer the further user a more advanced level of access to the implantable medical device than the first user interface; and
displaying the second user interface on the mobile computing device.

35. The non-transitory computer readable medium of claim 33, wherein the authentication process comprises a password-based authentication or a biometric-scan-based authentication.

36. The non-transitory computer readable medium of claim 33, wherein the steps further comprise:
receiving physiological data from a wearable medical device worn by a patient; and
communicating an alert in response to the received physiological data.

* * * * *